US011890340B2

(12) United States Patent
Fessler et al.

(10) Patent No.: US 11,890,340 B2
(45) Date of Patent: Feb. 6, 2024

(54) USE OF EPITHELIAL MEMBRANE PROTEIN 2 [EMP2] TARGETING AGENTS IN TREATING LUNG DISORDERS

(71) Applicant: The United States of America, as Represented By the Secretary, Department of Health and Human Services, Bethesda, MD (US)

(72) Inventors: Michael Brian Fessler, Cary, NC (US); Carmen J. Williams, Chapel Hill, NC (US); Wan-Chi Lin, Morrisville, NC (US)

(73) Assignee: The United States of America as Represented By The Secretary of the Department of Health and Human Services, Rockville, MD (US)

( * ) Notice: Subject to any disclaimer, the term of this patent is extended or adjusted under 35 U.S.C. 154(b) by 0 days.

(21) Appl. No.: 17/051,678

(22) PCT Filed: Apr. 30, 2019

(86) PCT No.: PCT/US2019/029801
§ 371 (c)(1),
(2) Date: Oct. 29, 2020

(87) PCT Pub. No.: WO2019/213020
PCT Pub. Date: Nov. 7, 2019

(65) Prior Publication Data
US 2021/0309737 A1    Oct. 7, 2021

Related U.S. Application Data

(60) Provisional application No. 62/771,326, filed on Nov. 26, 2018, provisional application No. 62/664,805, filed on Apr. 30, 2018.

(51) Int. Cl.
| | |
|---|---|
| *A61K 39/395* | (2006.01) |
| *A61K 31/713* | (2006.01) |
| *A61K 31/7088* | (2006.01) |
| *A61P 11/00* | (2006.01) |
| *C07K 16/28* | (2006.01) |
| *C07K 14/705* | (2006.01) |
| *C12N 15/113* | (2010.01) |
| *A61K 45/06* | (2006.01) |
| *A61K 39/00* | (2006.01) |
| *G01N 33/68* | (2006.01) |

(52) U.S. Cl.
CPC ...... *A61K 39/3955* (2013.01); *A61K 31/7088* (2013.01); *A61K 31/713* (2013.01); *A61P 11/00* (2018.01); *A61K 45/06* (2013.01); *A61K 2039/505* (2013.01); *C07K 14/705* (2013.01); *C07K 16/28* (2013.01); *C07K 2317/24* (2013.01); *C07K 2317/50* (2013.01); *C07K 2317/54* (2013.01); *C07K 2317/55* (2013.01); *C07K 2317/622* (2013.01); *C07K 2317/626* (2013.01); *C12N 15/113* (2013.01); *G01N 33/6893* (2013.01); *G01N 2333/47* (2013.01)

(58) Field of Classification Search
CPC .. A61K 39/3955; A61K 31/713; C07K 16/28; C07K 14/705; A61P 11/00
See application file for complete search history.

(56) References Cited

U.S. PATENT DOCUMENTS

| | | | |
|---|---|---|---|
| 2010/0272732 A1 | 10/2010 | Braun et al. | |
| 2013/0034555 A1* | 2/2013 | Gordon | A61P 31/10 424/135.1 |
| 2013/0344078 A1* | 12/2013 | Braun | C07K 16/30 435/7.1 |
| 2015/0079089 A1* | 3/2015 | Wadehra | A61P 5/14 424/139.1 |
| 2015/0329621 A1* | 11/2015 | Wadehra | A61P 35/00 424/139.1 |

FOREIGN PATENT DOCUMENTS

| | | |
|---|---|---|
| WO | 2013/119693 A1 | 8/2013 |
| WO | 2016/060407 A1 | 4/2016 |
| WO | WO-2017096397 A1 * | 6/2017 ......... A61K 47/6803 |

OTHER PUBLICATIONS

Benjamini et al, 1991. Immunology: A Short Course, 2nd edition, p. 40 only.*
Ferrara et al (2015. mAbs. 7(1): 32-41).*
Dahlin et al, 2004. Am J. Respir. Cell. Mol. Biol. 31: 309-316.*
Julia Klesney-Tait, et al., "Transepithelial migration of neutrophils into the lung requires TREM-1", The Journal of Clinical Investigation, Jan. 2013, pp. 138-149, vol. 123, No. 1.
Wan-Chi Lin, et al., "Epithelial Membrane Protein 2 Regulates Transepithelial Migration Of Neutrophils Into The Inflamed Airspace", American Journal of Respiratory and Critical Care Medicine, Abstract A5214, May 1, 2017, 1 page.
International Search Report for PCT/US2019/029801, dated Aug. 2, 2019 (PCT/ISA/210).
Written Opinion for PCT/US2019/029801, dated Aug. 2, 2019 (PCT/ISA/237).
Klesney-Tait, et al., "Transepithelial migration of neutrophils into the lung requires TREM-1", The Journal of Clinical Investigation, vol. 123, No. 1, Jan. 2013, pp. 138-149.

(Continued)

*Primary Examiner* — Zachary C Howard
(74) *Attorney, Agent, or Firm* — Sughrue Mion, PLLC

(57) ABSTRACT

Disclosed herein are methods of treating or preventing a lung disorder comprising administering to a subject a composition comprising an agent that modulates activity and/or expression of Epithelial Membrane Protein 2 (EMP2) in an amount effective to treat or prevent the lung disorder and compositions useful in such for methods.

11 Claims, 33 Drawing Sheets
Specification includes a Sequence Listing.

(56) References Cited

OTHER PUBLICATIONS

Lin, et al., "Epithelial Membrane Protein 2 Regulates Transepithelial Migration Of Neutrophils Into The Inflamed Airspace", American Journal of Respiratory and Critical Care Medicine, May 1, 2017, 1 page.

* cited by examiner

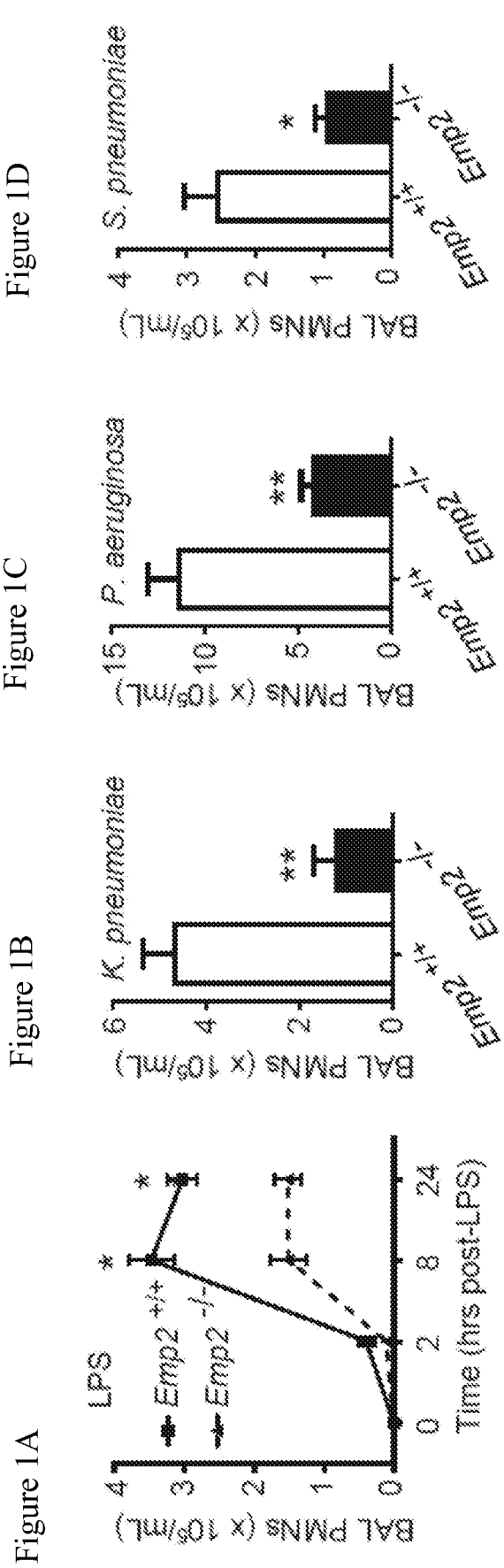

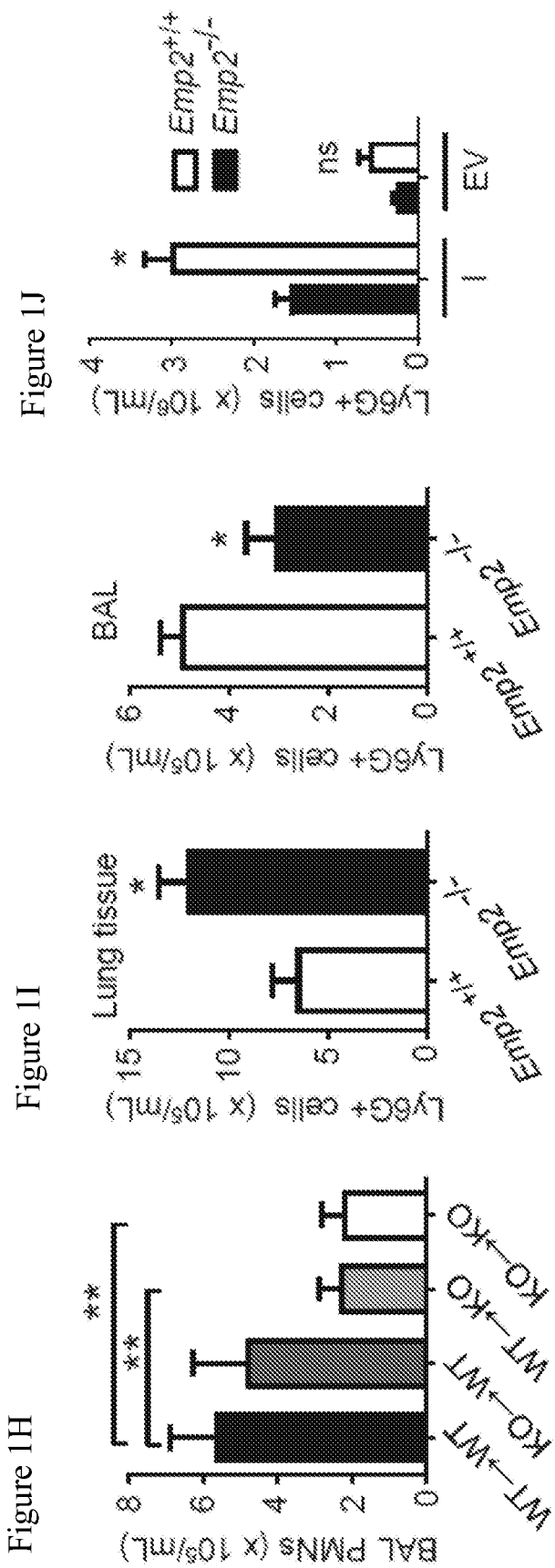

Figure 11

Mouse epithelial membrane protein 2 (mEMP2)

MLVILAFIIV FHIVSTALLF ISTIDNAWWV GDSFSADLWR VCTNSTNCTE

INELTGPEAF EGYSVMQAVQ ATMILSTILS CISFLIFLLQ LFRLKQGERF
                     Y136    Y144 Y146

VLTSIIQLMS CLCVMIGASI YTDRRQDLHQ QNRKLYYLLQ EGSYGYSFIL
  F159   Y165                 R
AWVAFAFTFI SGLMYMILRK RK

Transmembrane domains
Glycosylation sites
CRAC: (L/V)-$X_{1-5}$-(Y)-$X_{1-5}$-(K/R)
CARC: (K/R)-$X_{1-5}$-(Y/F)-$X_{1-5}$-(L/V)

| | | | | |
|---|---|---|---|---|
| Monocytes | CD45 + | Ly6G lo | CD11b hi; CD115 hi | CD88 lo |
| Recruited Mac | CD45 + | Ly6G lo | CD11b hi; CD115 hi | CD88 hi |
| Lymphocytes | CD45 + | CD19 hi OR CD3 hi | | |
| PMN | CD45 + | Ly6G hi | | |

Figure 15A
Figure 15B
☐ EMP2+/+_PBS
■ EMP2+/+_Bleo
▨ EMP2-/-_PBS
▨ EMP2-/-_Bleo
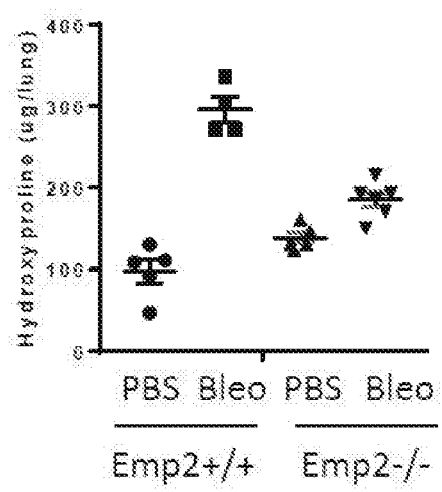
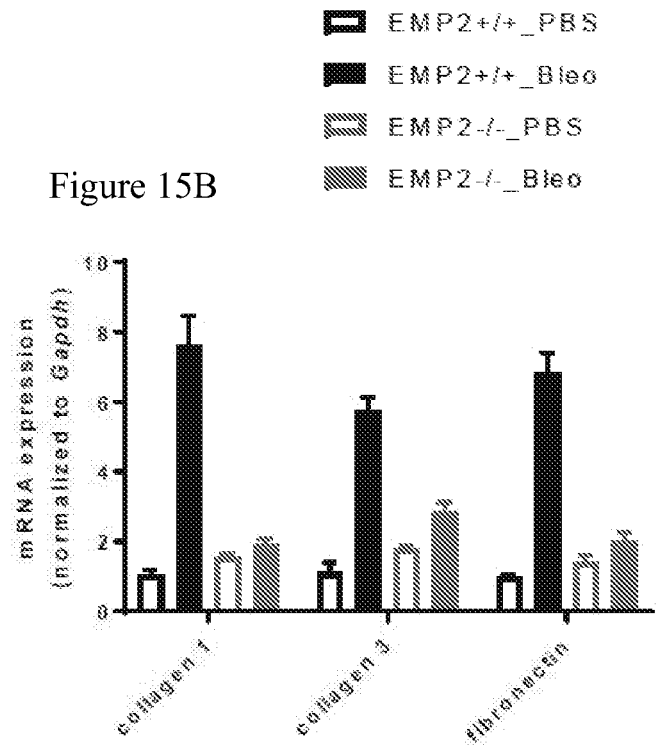
Figure 15C
Figure 15D
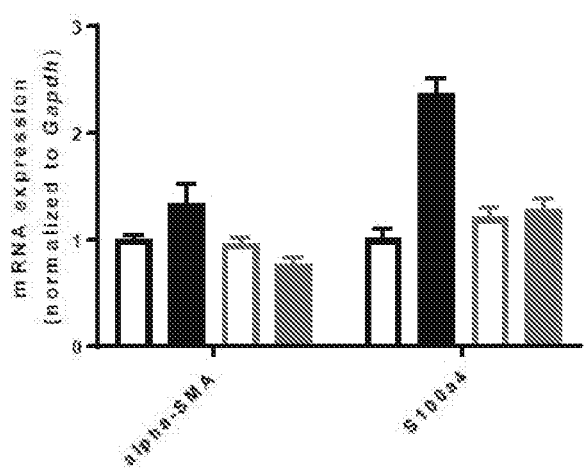
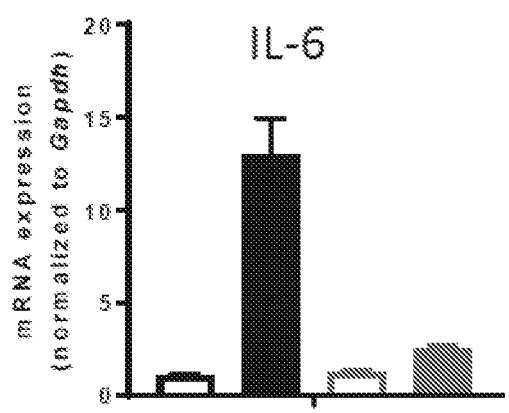

USE OF EPITHELIAL MEMBRANE PROTEIN 2 [EMP2] TARGETING AGENTS IN TREATING LUNG DISORDERS

CROSS REFERENCE TO RELATED APPLICATIONS

This application is a National Stage of International Application No. PCT/US2019/029801 filed Apr. 30, 2019, claiming priority based on U.S. Provisional Application Ser. No. 62/664,805, filed Apr. 30, 2018, and U.S. Provisional Application Ser. No. 62/771,326, filed Nov. 26, 2018, all of which are incorporated herein by reference in their entireties for all purposes.

GOVERNMENT SUPPORT

The federal government has certain rights in this invention.

FIELD OF INVENTION

The present invention relates to methods and compositions useful in treating lung disorders by targeting Epithelial Membrane Protein 2 (EMP2).

BACKGROUND OF THE INVENTION

Successful migration of polymorphonuclear neutrophils (PMNs) from the circulation to airway lumen is critical to pulmonary host defense, but also responsible for bystander tissue injury that underlies a wide array of acute and chronic lung diseases.

PMN trafficking to the lung differs fundamentally from that in other tissues (1). During pneumonia, PMNs responding to infection travel to the airspace lumen through a multi-step journey in which they first transit through the pulmonary capillary endothelium, then crawl through the extravascular matrix of the pulmonary interstitial space, cross through intercellular junctions between alveolar epithelial cells, and then finally access the airspace. Integrin-dependent firm adhesion to endothelium and diapedesis occur in alveolar capillaries, after which PMNs are thought to track along interstitial fibroblasts, finally passing paracellularly through the epithelium at the junction of alveolar epithelial type 1 (AT1) and type 2 (AT2) cells (2).

Studies over the past two decades have loosely categorized the PMN influx to different airway exposures on the basis of the PMN integrins utilized. Thus, trafficking to lipopolysaccharide (LPS), *E. coli*, and *P. aeruginosa* is primarily CD18 (β2 integrin)-dependent, whereas that to *S. pneumoniae* and CXCL1 is CD18-independent and CD29 (β1 integrin)-dependent (3). Endothelial ligands that interact with PMN integrins to control vascular egress have been well-described (3). Epithelial membrane proteins also regulate transepithelial migration (TEM) via cognate interactions with PMNs (4), and studies suggest that transepithelial, rather than transendothelial passage of PMNs is linked to epithelial wounding, catastrophic lung damage, and mortality (4, 5). Targeting pulmonary TEM might conceivably offer effective and selective strategies for PMN-mediated lung disease. However, the few epithelial membrane proteins implicated in pulmonary TEM to date (e.g., intercellular adhesion molecule [ICAM]-1; CD47; coxsackie and adenovirus receptor) have largely been extrapolated from in vitro studies of intestinal epithelium (4, 6). How and whether TEM-regulatory proteins are coordinated in alveolar epithelial cells (AECs) also remains an open question.

Although successful arrival of microbicidal PMNs to the airspace is essential for host defense against inhaled pathogens, PMN proteases and oxidants are well-known to cause severe bystander damage to structural cells in the lung (e.g., epithelial cells), thereby compromising gas exchange. Indeed, excessive accumulation of PMNs in the lung contributes to the pathogenesis of several prevalent lung disorders, among them, acute lung injury, bronchiectasis, and COPD. Unfortunately, to date, no drugs for controlling PMN accumulation in the lung have been successfully developed for human use. While some preclinical therapeutics target PMN chemotaxis broadly (e.g., chemokine receptor inhibitors), these agents have the potentially untoward effect of globally impairing PMN trafficking to all tissues. Targeting the molecular interactions between PMNs and pulmonary epithelial cells that govern the terminal entry of PMNs into the airspace—in particular, by identifying the lung epithelial cognate proteins that regulate this event—in principle carries promise as a strategy for selectively controlling PMN accumulation in the airspace.

Epithelial membrane protein 2 (EMP2) is a member of the tetraspan superfamily of membrane proteins. Although its mechanism of action remains somewhat obscure, EMP2, a lipid raft-localized protein, is thought to promote the recruitment of select integrins (α6β1, αvβ3), adhesion molecules (ICAM-1), and signaling proteins to plasma membrane raft microdomains, and to downregulate caveolin-1, thereby reciprocally augmenting rafts and reducing caveolae (7-10). Reports to date have largely focused on potential roles for EMP2 in cancer. In cancer cells, EMP2 may serve as a platform for integrin signaling, supporting cell adhesion to extracellular matrix (ECM) and other cytoskeletal functions (11). Remarkably, in both mouse and man, EMP2 is by far most highly expressed in lung. A prior report has clarified that within human and rodent lung, EMP2 is restricted to alveolar epithelial type 1 cells, barrier cells of the alveolar space that have largely been studied to date for their role in fluid/ion resorption. To date, however, no function has been assigned to EMP2 in lung biology.

SUMMARY OF THE INVENTION

The present invention is based, at least in part, on the finding that EMP2 functions as a regulator of AT1 membrane organization that instructs the terminal step of PMN traffic into the alveolus, and that targeting EMP2 offers a selective therapeutic strategy against lung diseases driven by excessive PMN delivery to the airspace.

In one aspect, the present invention includes a method of treating or preventing a lung disorder in a subject comprising administering to a subject in need thereof a composition comprising an agent that modulates the activity and/or expression of Epithelial membrane protein 2 (EMP2).

In another aspect, the present invention includes a composition comprising an agent that modulates the expression and/or activity of EMP2 and a pharmaceutically acceptable excipient for use in the treatment of a lung disorder.

In some embodiments, the agent may inhibit the activity and/or expression of EMP2. In some embodiments, the agent may be selected from a small molecule, a polypeptide, a polynucleotide, or combinations thereof.

In some embodiments, the agent may be an anti-EMP2 antibody. In some embodiments, the anti-EMP2 antibody may be a monoclonal antibody. In some embodiments, the anti-EMP2 antibody may be a human or humanized antibody. In some embodiments, the anti-EMP2 antibody may be an intact antibody. In some embodiments, the anti-EMP2 antibody may be a functional antibody fragment. In some embodiments, the anti-EMP2 antibody may be selected from Fab, F(ab')2, F(ab'), Fv, scFv, Fd, diabody, triabody or tretrabody. In some embodiments, the anti-EMP2 antibody fragment may be a single-chain variable fragment (scFv). In some embodiments, the anti-EMP2 antibody may be a diabody. In some embodiments, the anti-EMP2 antibody may be selected from the group consisting of PG101, ONCR-201, KS83, KS49, KS41, and KS89. In some embodiments, the anti-EMP2 antibody may be KS83.

In some embodiments, the agent may be a small interfering RNA (siRNA). In some embodiments, the agent may be an antisense oligonucleotide.

In some embodiments, the composition may be administered to the subject systemically. In some embodiments, the composition may be administered to the subject parenterally. In some embodiments, the composition may be administered to the subject topically, intranasally, intravenously, subcutaneously, intramuscularly, intradermally, or intraperitoneally. In some embodiments, the composition may be administered to the subject by inhalation. In some embodiments, the composition may be administered by a nebulizer or an inhaler. In some embodiments, the composition may be formulated as a nasal spray, gel, ointment, liquid, suspension, aerosol, tablet, pill or powder.

In some embodiments, the agent may be in an amount sufficient to reduce intra-airway leukocyte accumulation in the subject.

In some embodiments, the lung disorder may be a neutrophil-dependent lung disorder. In some embodiments, the composition may be administered to an infant at risk for acute lung injury due to meconium aspiration or prematurity.

In some embodiments, the lung disorder may be an epithelial lipid raft-dependent and/or caveolae-dependent lung disease. In some embodiments, the lung disorder may be a TGF-β mediated lung disorder, for example pulmonary fibrosis or acute lung injury. In some embodiments, the lung disorder may be an eosinophil-dependent lung disorder, for example asthma, acute eosinophilic pneumonia, or chronic eosinophilic pneumonia. In some embodiments, the lung disorder may be a monocyte-dependent lung disorder, for example lung fibrosis, or acute lung injury. In some embodiments, the lung disorder may be a lymphocyte-dependent lung disorder, for example lymphocytic interstitial pneumonia or lymphocytic bronchiolitis. In some embodiments, the lung disorder may comprise an epithelium-matrix interaction, for example idiopathic pulmonary fibrosis. In some embodiments, the lung disorder may be an acute disease, for example acute lung injury, acute respiratory distress syndrome, pneumonia, viral infection, or airway hyperresponsiveness. In some embodiments, the lung disorder may be a chronic disease, for example COPD, bronchiectasis, radiation- or chemotherapeutic-induced pneumonitis, idiopathic or induced interstitial lung disease, bronchopulmonary dysplasia, or lung fibrosis. In some embodiments, the lung disorder may be due to exposure to a toxic agent, for example. bioterroristic agent, an occupational hazardous agent or an environmental pollutant. In some embodiments, the lung disorder may be chemical pneumonitis due to chemical or acid or hydrocarbon aspiration. In some embodiments, the lung disorder may be chemical pneumonitis due to smoke inhalation.

In some embodiments, the present invention includes a kit comprising the composition. In some embodiments, the kit may be a therapeutic kit or a diagnostic kit.

In another aspect, the present invention includes a method to detect alveolar epithelial type 1 cell injury in lung disease in a subject by measuring the level of EMP2 protein in a sample obtained from the subject. In some embodiments, the sample may be plasma, serum or bronchoalveolar lavage fluid.

In another aspect, the present invention includes a method to target a molecule to alveolar epithelial type 1 cells comprising co-administering the molecule with an agent that binds EMP2.

BRIEF DESCRIPTION OF THE DRAWINGS

FIGS. 1A-1L illustrate that EMP2 regulates transepithelial migration of neutrophils into the alveolar lumen. $Emp2^{+/+}$ (wildtype or WT) and $Emp2^{-/-}$ (knockout or KO) mice received inhaled exposures to (A) LPS, (B) K. pneumoniae, (C) P. aeruginosa and (D) S. pneumoniae as shown and bronchoalveolar lavage (BAL) neutrophils (PMNs) were counted at various time points (A) or 24 h post-exposure. (B-D) (N=5-7/genotype). (E) BAL fluid (BALF) cytokines and chemokines were quantified 2 h post-LPS inhalation (N=11-12/genotype). (F) Mice were administered i.t. CXCL1 and BAL PMNs and BALF CXCL5 were quantified 4 h later (N=5-6/genotype). (G) Mice received i.p. CXCL1 and peritoneal lavage PMNs were quantified 4 h later (N=4/genotype). (H) Bone marrow chimeric mice were made by transfer of bone marrow cells from $Emp2^{+/+}$ (WT) or $Emp2^{-/-}$ (KO) donors to $Emp2^{+/+}$ or $Emp2^{-/-}$ irradiated recipients (Donor→Recipient). Chimeras were exposed to inhaled LPS, and BAL PMNs quantified 24 h later (N=3-6/chimera). (I) Eight hours post-LPS inhalation, $Ly6G^+$ PMNs were quantified by flow cytometry in lavaged and perfused lungs (left) and in the BAL (right) of $Emp2^{+/+}$ and $Emp2^{-/-}$ mice (N=4-5/genotype). (J) Pulmonary interstitial (I) and endovascular (EV) $Ly6G^+$ PMNs were quantified under similar conditions to those in panel I (N=4/genotype). (K) Live lung slices from $Emp2^{+/+}$ and $Emp2^{-/-}$ mice were stained for E-cadherin (epithelium), CD31 (endothelium), and Ly6G (PMNs) 6 h post-LPS. $Emp2^{-/-}$ lungs display an excess accumulation of peribronchovascular (interstitial) PMNs. Results are representative of N=3-4/genotype. (L) Human PMNs that transmigrated across a monolayer of scramble- or EMP2 shRNA-transduced Calu-3 cells in response to fMLP during a time course were quantified (N=3/condition/time point). Data are the mean±SEM and are representative of at least 3 independent experiments. *$P<0.05$, **$P<0.01$ by unpaired 2-tailed Student's test.

FIG. 11 shows the amino acid sequence of murine EMP2 protein (SEQ ID NO: 1). Putative transmembrane domains and glycosylation sites are shown. Manual inspection of the sequence suggests one putative cholesterol recognition amino acid consensus (CRAC) motif, and three putative reverse CRAC (CARC) sequences. Proposed consensus sequences for CRAC (SEQ ID NO: 2) and CARC (SEQ ID NO: 3) motifs are shown as reported (46, 47). Tyrosine (Y) residues changed to alanine by site-directed mutagenesis in our studies are identified.

FIGS. 15A-15D show that Emp2−/− mice have reduced lung fibrosis and pro-fibrotic gene expression changes in lung after inhaled bleomycin. Emp2+/+ and Emp2−/− mice were given 2 U/kg bleomycin or 1×PBS control intratracheally and sacrificed for lung analysis 21 days later. (A) Lung hydroxyproline (surrogate measure of collagen) was quantified using standard methods. (B-D) The indicated mRNA targets were quantified in lung by RT-qPCR, including (B) extracellular matrix genes, (C) markers of (myo)fibroblasts, and (D) the cytokine IL-6. N=5/genotype. SMA=smooth muscle actin.

DETAILED DESCRIPTION

Figures 1E, 1F, 1G:
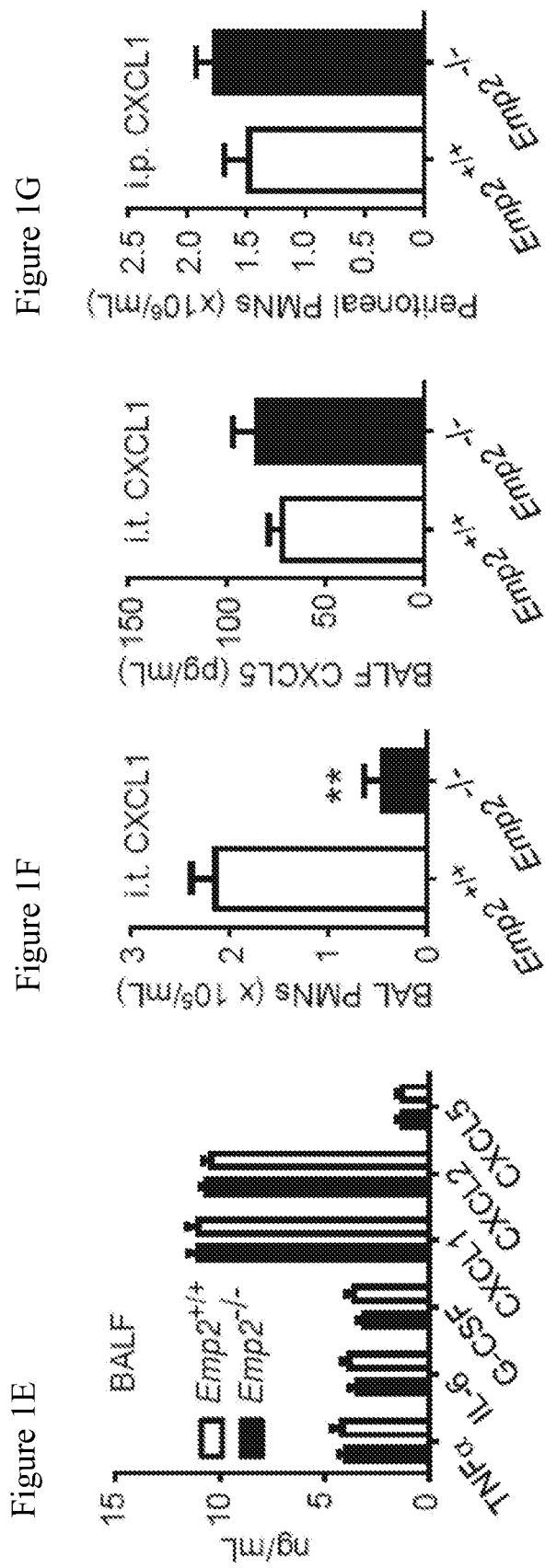

The present invention provides methods and compositions for treating or preventing lung disorders by administration of an agent that targets epithelial membrane protein 2 (EMP2).

The present invention is based, at least in part, on the novel insight that EMP2 functions as a regulator of AT1 membrane organization that instructs the terminal step of PMN traffic into the alveolus, and that targeting EMP2 offers a selective therapeutic strategy against lung diseases driven by excessive PMN delivery to the airspace. Epithelial membrane protein 2 (EMP2) is a member of the tetraspan superfamily of membrane proteins. In rodents and humans, EMP2 is by far most highly expressed in the lung, where it has been shown to be highly expressed in AT1 cells, but absent in AT2 cells and alveolar macrophages (AMs) (12). To date, however, no function has been assigned to EMP2 in lung biology, and few roles have been identified for AT1 cells in regulation of immune responses.

As reported herein, EMP2 has been identified as a regulator of AT1 membrane organization that instructs the terminal step of PMN traffic into the alveolus. Naive EMP2 knockout (KO) mice or Emp2−/− mice were found to have grossly normal lungs. However, Emp2−/− mice exhibited deficient alveolar polymorphonuclear neutrophils (PMN) influx in response to a wide range of CD18-dependent and -independent inhaled exposures arising from deficient PMN transepithelial migration (TEM). Flow cytometry and live lung slice imaging studies indicated that PMNs exit the pulmonary vasculature normally in Emp2−/− lungs, but collect in increased numbers in the pulmonary interstitial space due to reduced TEM into the airspace.

Emp2−/− AT1 cells displayed deficient lipid rafts and surface adhesion molecules and Emp2 deficient epithelial cells showed reduced PMN TEM in vitro. Mutagenesis of two putative cholesterol binding sequences in EMP2 indicated that EMP2 serves a critical raft scaffolding function. For example, EMP2-silenced Calu-3 cells (a human airway epithelial cell line) showed reduced transmigration of human PMNs in vitro. Both primary EMP2 −/− alveolar epithelial cells and EMP2-silenced Calu-3 cells displayed reduced lipid rafts and abnormal surface levels of integrins and other adhesion molecules, indicating that EMP2 deficiency attenuates cell surface display of multiple adhesion-related proteins. Inspection of the amino acid sequence of EMP2 indicated the presence of a cholesterol recognition amino acid consensus (CRAC) motif, as well as a CARC (i.e., reverse CRAC) motif. CRAC and CARC domains are proposed to mediate protein binding to cholesterol, and have been identified and confirmed in select membrane proteins, but not previously identified/investigated in EMP2. It was found that, whereas transfection of wild type EMP2 into EMP2−/−Let1 epithelial cells increases raft abundance (cholera toxin B binding), transfection of EMP2 with mutagenized CRAC or CARC sequence does not increase raft signal, supporting the role of CRAC and CARC sequences of EMP2 in the raft-supporting function of EMP2. The presence of these sequences in EMP2 indicates that EMP2 may bind cholesterol directly in its role as a raft scaffolding protein; and interventions upon these sequences (e.g., through mutagenesis, peptides, or small molecules) may inhibit EMP2 membrane organizing function through targeting its binding to cholesterol.

Remarkably, Emp2−/− mice had reduced lung injury and, despite reduced arrival of PMNs in the airspace, Emp2−/− mice had enhanced survival during bacterial pneumonia. Without wishing to be bound by theory, it is proposed that this is due to reduced extrapulmonary bacterial dissemination (i.e. septicemia) due to a more intact lung epithelial barrier due to reduced PMN-mediated epithelial injury and/or due to reduced respiratory failure due to a more intact lung epithelial barrier. Furthermore, upon exposure to bleomycin inhalation, which is a DNA-damaging agent used to model severe lung injury and fibrosis, Emp2−/− mice were protected from weight loss, had reduced influx of leukocytes into airspace, reduced pro-inflammatory cytokines and markers of microvascular injury in the airspace, and reduced lung fibrosis and pro-fibrotic gene expression changes in the lung.

Additionally, wild type mice that were pretreated intratracheally with an agent specifically targeting EMP2, such as anti-EMP2 antibody, and then exposed to LPS aerosol, also showed reduction in airspace neutrophils 24 h post-LPS inhalation compared to controls. This indicates that targeting EMP2 by an anti-EMP2 agent successfully reduces lung inflammation and provides a protective benefit in a normal (i.e., "wild type") mouse.

Thus, EMP2 represents a target for reduction of intra-airway PMN accumulation during lung disease, and also for pulmonary epithelial bather protection. Given that EMP2 broadly regulates surface expression of lipid rafts and several signaling proteins, targeting it with an anti-EMP agent is effective in reducing PMN transit and protecting the respiratory epithelium in a wide variety of disease exposure contexts. As several respiratory viruses enter epithelial cells via lipid rafts (e.g., influenza A, RSV), EMP2 targeting would also inhibit viral pathogenesis in the lung through neutrophil-independent mechanisms. The finding that EMP-deficient mice have improved survival during bacterial pneumonia indicates that EMP2 targeting is not deleterious during lung infection, and, indeed, is beneficial. The remarkable cell type specificity of EMP2 indicates that its targeting would have limited effects in other tissues. Nonetheless, the accessibility of EMP2 to the airway lumen also indicates that EMP2 can be targeted by various administration routes, including topical applications via direct targeting in the airway (for example, with nebulized agents). Accordingly, targeting EMP2 provides an effective approach for treating or ameliorating or preventing lung disorders.

In one aspect, the present invention provides a method of treating or preventing a lung disorder in a subject by administering to the subject a composition comprising an agent that modulates the activity and/or expression of EMP2.

In another aspect the present invention includes a composition comprising an agent that modulates the activity and/or expression of EMP2 and a pharmaceutically acceptable excipient for use in the treatment of a lung disorder.

EMP2 has been isolated from a variety of species including without limitation human, baboon, rhesus macaque, chimpanzee, bovine, dog, horse, rabbit, mouse, rat, guinea pigs and zebra fish, and its amino acid sequences as well as encoding nucleotide sequences are known. See e.g. GENBANK accession numbers NM_001424.5 (human), NM_001265948.1 (rhesus macaque), NM_001105239.1 (chimpanzee), NM_001075324.1 (bovine), NM007929.2 (mouse), NM_001007721.1 (rat), NM_001004119.1 (zebrafish).

The term EMP2 refers to an EMP2 protein isolated from any species, or a homolog or variant thereof. The term EMP2 also includes any post-translationally modified versions of an EMP2 primary amino acid sequence, including but not limited to phosphorylation, glycosylation, methylation, acetylation, myristoylation, prenylation, palmitation, amidation, etc.

As used herein, the term "homolog" is used to refer to a protein or peptide which differs from a naturally occurring protein or peptide (i.e., the "wild-type" protein) by minor modifications to the naturally occurring protein or peptide, but which maintains the basic protein and side chain structure of the naturally occurring form. Such changes include, but are not limited to: changes in one or a few amino acid side chains; changes one or a few amino acids, including deletions (e.g., a truncated version of the protein or peptide) insertions and/or substitutions; changes in stereochemistry of one or a few atoms; and/or minor derivatizations, including but not limited to: methylation, glycosylation, phosphorylation, acetylation, myristoylation, prenylation, palmitation, amidation. A homolog of a given protein may comprise, consist essentially of, or consist of, an amino acid sequence that is at least about 45%, or at least about 50%, or at least about 55%, or at least about 60%, or at least about 65%, or at least about 70%, or at least about 75%, or at least about 80%, or at least about 85%, or at least about 90%, or at least about 95% identical, or at least about 95% identical, or at least about 96% identical, or at least about 97% identical, or at least about 98% identical, or at least about 99% identical (or any percent identity between 45% and 99%, in whole integer increments), to the amino acid sequence of the reference protein. In one embodiment, the homolog comprises, consists essentially of, or consists of, an amino acid sequence that is less than 100% identical, less than about 99% identical, less than about 98% identical, less than about 97% identical, less than about 96% identical, less than about 95% identical, and so on, in increments of 1%, to less than about 70% identical to the naturally occurring amino acid sequence of the reference protein.

The term "agent" refers to a compound or molecule that is known or thought to modulate or change (increase or decrease) the expression and/or activity of EMP2. In some embodiments, the agent may increase, enhance or upregulate the activity and/or expression of EMP2. In some embodiments, the agent may decrease, inhibit or downregulate the activity and/or expression of EMP2. Embodiments include but are not limited to small molecules, polypeptides, polynucleotides or combinations thereof.

For example, in some embodiments, the agent may be a small molecule such as a drug molecule that modulates the activity and/or expression of EMP2. In some embodiments, the small molecule agent decreases, inhibits or downregulates the activity and/or expression of EMP2.

In some embodiments, the agent may be a polypeptide, that modulates the activity and/or expression of EMP2. The term "polypeptide" refers to a chain of amino acids that contains at least two amino acids and may be used to mean peptides, oligopeptides, polypeptides or proteins. Protein fragments, analogues, mutated or variant proteins, fusion proteins, and the like, are also included within the meaning of the term. In some embodiments, the polypeptide agent decreases, inhibits or downregulates the activity and/or expression of EMP2.

For example, in some embodiments, the polypeptide may be an anti-EMP2 antibody. Antibodies useful in the invention include any antibody capable of binding EMP2 or a post-translationally modified EMP2, such as phosphorylated or glycosylated EMP2.

Antibodies suitable for use in the present invention include serum containing such antibodies, or antibodies that have been purified to varying degrees.

In some embodiments, the antibody selectively binds EMP2. An antibody encompassed by the present invention includes any antibody that selectively binds to a conserved binding surface or epitope of EMP2 protein. As used herein, an "epitope" of a given protein or peptide or other molecule is generally defined, with regard to antibodies, as a part of or a site on a larger molecule to which an antibody or antigen-binding fragment thereof will bind, and against which an antibody will be produced. The term epitope can be used interchangeably with the term "antigenic determinant," "antibody binding site," or "conserved binding surface" of a given protein or antigen. More specifically, an epitope can be defined by both the amino acid residues involved in antibody binding and also by their conformation in three dimensional space (e.g., a conformational epitope or the conserved binding surface). An epitope can be included in peptides as small as about 4-6 amino acid residues, or can be included in larger segments of a protein, and need not be comprised of contiguous amino acid residues when referring to a three dimensional structure of an epitope, particularly with regard to an antibody-binding epitope. Antibody-binding epitopes are frequently conformational epitopes rather than a sequential epitope (i.e., linear epitope), or in other words, an epitope defined by amino acid residues arrayed in three dimensions on the surface of a protein or polypeptide to which an antibody binds. As mentioned above, the conformational epitope is not comprised of a contiguous sequence of amino acid residues, but instead, the residues are perhaps widely separated in the primary protein sequence, and are brought together to form a binding surface by the way the protein folds in its native conformation in three dimensions.

As used herein, the term "selectively binds" refers to the specific binding of one protein to another (e.g., an antibody, fragment thereof, or binding partner to an antigen), wherein the level of binding, as measured by any standard assay (e.g., an immunoassay), is statistically significantly higher than the background control for the assay. For example, when performing an immunoassay, controls typically include a reaction well/tube that contain antibody or antigen binding fragment alone (i.e., in the absence of antigen), wherein an amount of reactivity (e.g., non-specific binding to the well) by the antibody or antigen binding fragment thereof in the absence of the antigen is considered to be background. Binding can be measured using a variety of methods standard in the art, including, but not limited to: Western blot, immunoblot, enzyme-linked immunosorbant assay (ELISA), radioimmunoassay (RIA), immunoprecipitation, surface plasmon resonance, chemiluminescence, fluorescent polarization, phosphorescence, immunohistochemical analysis, matrix-assisted laser desorption/ionization time-of-flight (MALDI-TOF) mass spectrometry, microcytometry, microarray, microscopy, fluorescence activated cell sorting (FACS), and flow cytometry.

As used herein, the term "antibody" includes an intact antibody (or full length antibody or whole antibody). An intact antibody refers to an antibody having a structure substantially similar to a native antibody structure or having heavy chains that contain an Fc region.

As used herein, the term "antibody" means not only intact antibody molecules, but also functional fragments of antibody molecules that retain immunogen-binding ability. Such fragments are well known in the art, and may lack the Fc fragment of intact antibody, clear more rapidly from the circulation, and have less non-specific tissue binding of an intact antibody (Wahl et al., J. Nucl. Med. 24:316 325 (1983).

Thus, the term "antibody" may refer to a protein that includes at least one immunoglobulin variable domain or immunoglobulin variable domain sequence. For example, an antibody may include a heavy (H) chain variable region (abbreviated herein as $V_H$), and a light (L) chain variable region (abbreviated herein as $V_L$), or two heavy (H) chain variable regions and two light (L) chain variable regions. For example, an antibody may be a tetramer of two heavy immunoglobulin chains and two light immunoglobulin chains, wherein the heavy and light immunoglobulin chains are inter-connected by, e.g., disulfide bonds. The $V_H$ and $V_L$ regions can be further subdivided into regions of hypervariability, termed "complementarity determining regions" ("CDR"), interspersed with regions that are more conserved, termed "framework regions" ("FR"). Each $V_H$ and $V_L$ is typically composed of three CDRs and four FRs, arranged from amino-terminus to carboxy-terminus in the following order: FR1, CDR1, FR2, CDR2, FR3, CDR3, FR4. The $V_H$ or $V_L$ chain of the antibody can further include all or part of a heavy or light chain constant region, to thereby form a heavy or light immunoglobulin chain, respectively. An antibody can have the structural features of IgA, IgG, IgE, IgD, IgM (as well as subtypes thereof). In IgGs, the heavy chain constant region includes three immunoglobulin domains, CH1, CH2 and CH3. The light chain constant region includes a CL domain. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system. The light chains of the immunoglobulin may be of types kappa or lambda.

The term "antibody" also encompasses functional fragments of intact antibodies that retain the ability to specifically bind to a EMP2. Examples of functional antibody fragments include, without limitation, Fab fragment, a monovalent fragment consisting of the $V_L$, $V_H$, $C_L$ and $C_{H1}$ domains; F(ab')$_2$ fragment, a bivalent fragment comprising two Fab fragments linked by a disulfide bridge at the hinge region; F(ab') fragment, a monovalent fragment produced by reduction of F(ab')$_2$ which has a free sulfhydryl group; Fd fragment comprising the $V_H$ and Cm domains; Fv fragment comprising the $V_L$ and $V_H$ domains of a single arm of an antibody; or an isolated complementarity determining region (CDR) that retains functionality.

Furthermore, although the two domains of the Fv fragment, $V_L$ and $V_H$, are encoded by separate genes, they can be joined, using recombinant methods, by a synthetic linker that enables them to be made as a single protein chain in which the $V_L$ and $V_H$ regions pair to form monovalent molecules known as single chain Fv (scFv). See e.g., Bird et al. (1988) Science 242:423-426; and Huston et al. (1988) Proc. Natl. Acad. Sci. USA 85:5879-5883.

Further, divalent or bivalent scFvs (di-scFvs or bi-scFvs) may be engineered by linking two scFvs in within a single peptide chain known as a tandem scFv which contains two $V_H$ and two $V_L$ regions. ScFv dimers and higher multimers may also be created using linker peptides of fewer than 10 amino acids that are too short for the two variable regions to fold together, which forces the scFvs to dimerize and produce diabodies or form other multimers. Diabodies have been shown to bind to their cognate antigen with much higher affinity than the corresponding scFvs, having dissociation constants up to 40-fold lower than the $K_D$ values for the scFvs. Another form of diabody is single-chain (Fv)$_2$ in which two scFv fragments may be covalently linked to each other. Very short linkers (such as ≤3 amino acids) lead to the formation of trivalent triabodies or tetravalent tetrabodies that exhibit even higher affinities for to their antigens than diabodies. Other variants include minibodies, which are scFv-$C_{H3}$ dimers, and larger scFv-Fc fragments (scFv-$C_{H2}$-$C_{H3}$ dimers), and even an isolated CDR may exhibit antigen-binding function. All of these fragments of antibodies, proteolytic or engineered, and related variants are intended to be encompassed within the term "antibody fragment".

Other functional aspects of an immunoglobulin molecule include the valency of an immunoglobulin molecule, the affinity of an immunoglobulin molecule, and the avidity of an immunoglobulin molecule. As used herein, affinity refers to the strength with which an immunoglobulin molecule binds to an antigen at a single site on an immunoglobulin molecule (i.e., a monovalent Fab fragment binding to a monovalent antigen). Affinity differs from avidity, which refers to the sum total of the strength with which an immunoglobulin binds to an antigen. As used herein, valency refers to the number of different antigen binding sites per immunoglobulin molecule (i.e., the number of antigen binding sites per antibody molecule of antigen binding fragment).

Antibodies and functional fragments thereof useful in the present invention, include without limitation, bispecific antibodies, chimeric antibodies, fusion polypeptides, nanobodies, linear antibodies (Zapata et al., Protein Eng. 8(10): 1057-1062, 1995), single domain antibodies, single chain antibodies, antibodies having multiple valencies (e.g., diabodies, tribodies, tetrabodies, and pentabodies etc.).

Antibodies useful in the present invention may be humanized. Humanized antibodies are molecules having an antigen binding site derived from an immunoglobulin from a non-human species, the remaining immunoglobulin-derived parts of the molecule being derived from a human immunoglobulin. The antigen binding site may comprise either complete variable regions fused onto human constant domains or only the complementarity determining regions (CDRs) grafted onto appropriate human framework regions in the variable domains. Humanized antibodies can be produced, for example, by modeling the antibody variable domains, and producing the antibodies using genetic engineering techniques, such as CDR grafting. Techniques to humanize antibodies are particularly useful when non-human animal (e.g., murine) antibodies are generated. A description of various techniques for the production of humanized antibodies is found, for example, in Morrison et al. (1984) Proc. Natl. Acad. Sci. USA 81:6851-55; Whittle et al. (1987) Prot. Eng. 1:499-505; Co et al. (1990) J. Immunol. 148:1149-1154; Co et al. (1992) Proc. Natl. Acad. Sci. USA 88:2869-2873; Carter et al. (1992) Proc. Natl. Acad. Sci. 89:4285-4289; Routledge et al. (1991) Eur. J. Immunol. 21:2717-2725.

Antibodies useful in the present invention also include human antibodies, which may be fully or effectively human in nature. One method to produce such antibodies having a particular binding specificity includes obtaining human antibodies from immune donors (e.g., using EBV transformation of B-cells or by PCR cloning and phage display). In addition, and more typically, synthetic phage libraries have been created which use randomized combinations of synthetic human antibody V-regions. By selection on antigen, human (or fully human) antibodies can be made in which it is assumed the V-regions are very human like in nature. Phage display libraries are described in more detail below. Finally, fully human antibodies can be produced from transgenic mice. Specifically, transgenic mice have been created which have a repertoire of human immunoglobulin germline gene segments. Therefore, when immunized, these mice produce human like antibodies.

Antibodies useful in the present invention may be genetically engineered antibodies produced by standard recombinant DNA techniques involving the manipulation and re-expression of DNA encoding antibody variable and/or constant regions. Particular examples include, chimeric antibodies, where the $V_H$ and/or $V_L$ domains of the antibody come from a different source as compared to the remainder of the antibody, and CDR grafted antibodies (and antigen binding fragments thereof), in which at least one CDR sequence and optionally at least one variable region framework amino acid is (are) derived from one source and the remaining portions of the variable and the constant regions (as appropriate) are derived from a different source.

Methods of preparing antibodies are well known in the art. One method of obtaining antibodies is to immunize suitable host animals with an immunogen and to follow standard procedures for polyclonal or monoclonal antibody production. The immunogen will facilitate presentation of the immunogen on the cell surface Immunization of a suitable host can be carried out in a number of ways known in the art. Typically, a host animal, such as, for example, but not limited to, a rabbit, a sheep, a hamster, a guinea pig, a mouse, a rat, or a chicken, is exposed to or immunized with an effective amount of antigen against which an antibody is desired by injecting the antigen into the animal. An effective amount of antigen refers to an amount needed to induce antibody production by the animal. The animal's immune system is then allowed to respond over a pre-determined period of time. The immunization process can be repeated until the immune system is found to be producing antibodies to the antigen.

In order to obtain polyclonal antibodies specific for the antigen, serum is collected from the animal that contains the desired antibodies (or in the case of a chicken, antibody can be collected from the eggs). Such serum is useful as a reagent. Polyclonal antibodies can be further purified from the serum (or eggs) by, for example, treating the serum with ammonium sulfate.

Monoclonal antibodies may be produced according to the methodology of Kohler and Milstein (Nature 256:495-497, 1975), or using the human B-cell hybridoma method, Kozbor, J., Immunol, 133:3001 (1984); Brodeur et al., Monoclonal Antibody Production Techniques and Applications, pp. 51-63 (Marcel Dekker, Inc., New York, 1987). For example, B lymphocytes are recovered from the spleen (or any suitable tissue) of an immunized animal and then fused with myeloma cells to obtain a population of hybridoma cells capable of continual growth in suitable culture medium. Hybridomas producing the desired antibody are selected by testing the ability of the antibody produced by the hybridoma to bind to the desired antigen. The hybridomas may be cloned and the antibodies may be produced by and then isolated from the hybridomas. A preferred method to produce antibodies of the present invention includes (a) administering to an animal an effective amount of a protein or peptide to produce the antibodies and (b) recovering the antibodies. As used herein, the term "monoclonal antibody" includes chimeric, humanized, and human forms of a monoclonal antibody. Monoclonal antibodies are often synthesized in the laboratory in pure form by a single clone (population) of cells. These antibodies can be made in large quantities and have a specific affinity for certain target antigens which can be found on the surface of cells.

Antibodies of the present invention may also be produced recombinantly. For example, once a cell line, for example a hybridoma, expressing an antibody has been obtained, it is possible to clone therefrom the cDNA and to identify the variable region genes encoding the desired antibody, including the sequences encoding the CDRs. From here, antibodies and antigen binding fragments may be obtained by preparing one or more replicable expression vectors containing at least the DNA sequence encoding the variable domain of the antibody heavy or light chain and optionally other DNA sequences encoding remaining portions of the heavy and/or light chains as desired, and transforming/transfecting an appropriate host cell, in which production of the antibody will occur. Suitable expression hosts include bacteria, (for example, an *E. coli* strain), fungi, (in particular yeasts, e.g. members of the genera *Pichia, Saccharomyces,* or *Kluyveromyces,*) and mammalian cell lines, e.g. a non-producing myeloma cell line, such as a mouse NSO line, or CHO cells. Particular methods for producing antibodies in this way are generally well known and routinely used. For example, basic molecular biology procedures are described by Maniatis et al. (Molecular Cloning, Cold Spring Harbor Laboratory, New York, 1989); DNA sequencing can be performed as described in Sanger et al. (PNAS 74:5463, (1977)) and the Amersham International plc sequencing handbook; and site directed mutagenesis can be carried out according to the method of Kramer et al. (Nucl. Acids Res. 12, 9441, (1984)) and the Anglian Biotechnology Ltd. handbook. Additionally, there are numerous publications detailing techniques suitable for the preparation of antibodies by manipulation of DNA, creation of expression vectors and transformation of appropriate cells, for example as reviewed by Mountain A and Adair, J R in Biotechnology and Genetic Engineering Reviews (ed. Tombs, M P, 10, Chapter 1, 1992, Intercept, Andover, UK).

In some embodiments, the anti-EMP2 antibody is a monoclonal antibody. In some embodiments, the anti-EMP2 antibody is a human or humanized antibody. In some embodiments, the anti-EMP2 antibody may be an intact or full length or whole antibody. In some embodiments, the anti-EMP2 antibody may be a functional antibody fragment. In some embodiments, the anti-EMP2 antibody may be selected from Fab, F(ab')2, F(ab'), Fv, scFv, Fd, diabody, triabody or tretrabody. In some embodiments, the anti-EMP2 antibody fragment may be a single-chain variable fragment (scFv). In some embodiments, the anti-EMP2 antibody is a diabody.

A number of anti-EMP2 antibodies are available and may be used in the present invention. Examples include without limitation, anti-human EMP2 antibodies KS83, PG101, KS49, KS41 and KS89 (all commercially available from Creative Biolabs, Shirley, N.Y. 11967), and ONCR-201 (developed by Paganini Biopharma., now acquired by Onco Response, Houston, Tex. 77024).

In some embodiments, the agent may be a polynucleotide. The term "polynucleotide" refers to a deoxyribonucleic acid (DNA) molecule or ribonucleic acid (RNA) molecule of any suitable length that modulates the activity and/or expression of EMP2. The term "polynucleotide" refers to oligonucleotides or polynucleotides. In some embodiments, the polynucleotide agent decreases, inhibits or downregulates the activity and/or expression of EMP2.

In some embodiments, when administered to a cell, a polynucleotide agent may lead to a decrease (e.g., by 10%, 25%, 50%, 75%, or even 90-100%) in the expression of the gene encoding the EMP protein. Embodiments include, without limitation, a single or double-stranded RNA, siRNA (short interfering RNA), shRNA (short hairpin RNA), or antisense RNA, or a portion thereof, or a mimetic thereof. Typically, a polynucleotide agent comprises or corresponds to at least a portion of a target nucleic acid molecule, or an ortholog thereof, or comprises at least a portion of the complementary strand of a target nucleic acid molecule.

In some embodiments, the agent is an siRNA. The term "siRNA" refers to small or short interfering RNA. A siRNA is a double stranded RNA that corresponds to or matches a reference or target gene sequence. This matching need not be perfect so long as each strand of the siRNA is capable of binding to at least a portion of the target sequence. siRNA can be used to inhibit gene expression, see for example Bass, 2001, Nature, 411, 428 429; Elbashir et al., 2001, Nature, 411, 494 498; and Zamore et al., Cell 101:25-33 (2000). EMP2 siRNAs are commercially available, for example human EMP2 siRNA (s4654, s4656, s4655), mouse EMP2 siRNA (s65478, s65479, s65477) and rat EMP2 siRNA (s165667, s165668, s165669) available from Ambion™ In Vivo Pre-designed siRNAs (Catalog No. 4457308), ThermoFisher Scientific.

In some embodiments, the agent is an antisense polynucleotide. The term "antisense polynucleotide" refers to a nucleic acid molecule that binds to target RNA by means of RNA-RNA or RNA-DNA interactions and alters the activity of the target RNA (for a review, see Stein et al. 1993; Woolf et al., U.S. Pat. No. 5,849,902). Typically, antisense molecules are complementary to a target sequence along a single contiguous sequence of the antisense molecule. However, in certain embodiments, an antisense molecule can bind to a target sequence such that the target molecule forms a loop, and/or an antisense molecule can bind such that the antisense molecule forms a loop. Thus, the antisense molecule can be complementary to two (or even more) non-contiguous target sequences or two (or even more) non-contiguous sequence portions of an antisense molecule can be complementary to a target sequence or both. For a review of current antisense strategies, see Schmajuk N A et al., 1999; Delihas N et al., 1997; Aboul-Fadl T, 2005). The EMP2 gene sequences may be used, for example, in the discovery and development of therapeutic antisense polynucleotides to decrease the expression of EMP2.

Embodiments also include catalytic RNA molecules or ribozymes. Such catalytic RNA molecules can be used to inhibit expression of an EMP2 encoding nucleic acid molecule in vivo. The inclusion of ribozyme sequences within an antisense RNA confers RNA-cleaving activity upon the molecule, thereby increasing the activity of the constructs. The design and use of target RNA-specific ribozymes is described in Haseloff et al., Nature 334:585-591 (1988).

In certain embodiments, the agent may be administered in combination with an additional therapeutic agent, i.e. it may be co-administered or sequentially administered with an additional therapeutic agent for treating the lung disorder.

In some embodiments, the composition of the present invention may further include a pharmaceutically acceptable carrier (including an excipient, diluent, adjuvant or delivery vehicle). The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Common suitable pharmaceutical carriers are described in "Remington's Pharmaceutical Sciences" by E. W. Martin.

Compositions comprising an agent may be administered locally or systemically. Compositions may be administered by any suitable route, including without limitation, topical, oral, subcutaneous, intravenous, intramuscular, intradermal, transdermal, or intraperitoneal. The composition may formulated for intranasal or pulmonary administration to provide required levels of the composition to the subject. The composition may be administered by any suitable method, including but not limited to, inhalation, topical application, injection, or oral ingestion. The composition may be formulated in a pharmaceutically-acceptable buffer such as physiological saline. Dosage forms may include, for example, nasal sprays, nasal droplets, liquids, gels, ointments, creams, suspensions, solutions, aerosols, tablets, pills, powder capsules, patches, or the like.

In some embodiments, the composition may be administered via inhalation. In some embodiments, it may be administered by means of a nebulizer or an inhaler (e.g., manually-actuated pressurized metered-dose inhaler, breath-actuated pressurized metered-dose inhaler, dry powder inhaler, mist inhaler) or the like.

The agent is administered in an amount sufficient to reduce intra-airway accumulation of leukocytes in the subject. The term leukocytes includes neutrophils, monocytes and monocyte derived macrophages, lymphocytes and eosinophils.

The precise amount of the agent to be administered varies depending upon the manner of administration, the age and body weight of the patient, and with the clinical symptoms of the lung disorder, as well as other factors that will be generally known in the art. Human dosage amounts can initially be determined by extrapolating from the amount of the agent used in mice, as a skilled artisan recognizes it is routine in the art to modify the dosage for humans compared to animal models.

The methods and compositions of the present invention are suitable in the treatment or prevention of a wide variety of lung disorders. The terms "treatment," "treating" and the like mean obtaining a desired pharmacologic and/or physiologic effect. Treatment includes inhibiting a disease, (e.g., arresting its development) and relieving a disease (e.g., reducing symptoms associated with a disease). Treatment as used herein covers any administration of a pharmaceutical agent or compound to an individual to treat, cure, alleviate, improve, diminish, inhibit or ameliorate a condition in the individual. The terms "prevention," "preventing" and like mean treating prophylactically or reducing the frequency of occurrence of a disease or the severity of the disease by administering an agent prior to appearance of a symptom of that disease. The prophylactic treatment may completely prevent or reduce appearance of the disease or a symptom thereof and/or may be therapeutic in terms of a partial or complete cure for a disease and/or adverse effect attributable to the disease. Prophylactic treatment may include reducing or preventing a disease or condition (e.g., preventing a lung disorder) from occurring in an individual who may be predisposed to the disease but has not yet been diagnosed as having it.

Compositions of the present invention can be administered on a chronic or an acute basis. For example, when treating chronic conditions, such as for example, cystic fibrosis, a composition can be administered as a standing drug that is given daily or on some other periodic basis. Alternatively, patients with chronic conditions may be treated according to the present invention by administration of compositions at the outset of exacerbations or flare-ups of the condition on an acute dosing basis until the exacerbated symptoms are controlled. Similarly, patients with acute conditions such as acute respiratory distress syndrome (ARDS) can be treated according to the present invention at the outset of the condition to relieve symptoms thereof.

As shown herein in Examples 2 and 6, EMP2 deletion in mice leads to a reduced influx of neutrophils. Further, as shown in Example 3, the reduced influx of neutrophils is due to dysregulation of expression of adhesion molecules CD47, CAM-1 and β3 integrin present in the epithelium. Since the influx of monocytes, eosinophils and lymphocytes into airspace is also dependent upon interaction with these same adhesion molecules, deletion of EMP2 would reduce the influx of these cells as well. Indeed, as shown in Example 6, Emp2−/− mice exhibit a reduction in the airspace of monocytes and monocyte-derived ('recruited') alveolar macrophages.

Thus, in some embodiments, the lung disorder may be a neutrophil-dependent lung disorder and administration of the agent reduces intra-airway accumulation of neutrophils in the subject. Examples of neutrophil-dependent lung disorders include, without limitation, acute lung injury/acute respiratory distress syndrome, asthma, pneumonia, bronchitis, chronic bronchitis and bronchiectasis. In some embodiments, the lung disorder may be an eosinophil-dependent lung disorder. Examples include, without limitation, asthma, acute eosinophilic pneumonia, and chronic eosinophilic pneumonia. In some embodiments, the lung disorder may be a monocyte-dependent or macrophage-dependent lung disorder. Examples include, without limitation, lung fibrosis, acute lung injury. In some embodiments, the lung disorder may be a lymphocyte-dependent lung disorder. Examples include, without limitation, lymphocytic interstitial pneumonia and lymphocytic bronchiolitis.

As demonstrated herein in Example 4, EMP2 is required for epithelial lipid raft integrity and EMP2 deletion leads to a decrease in epithelial lipid raft mass. Accordingly, in some embodiments, the lung disorder is an epithelial lipid raft-dependent and/or caveolae-dependent lung disease. Examples of such lung disorders, in which lipid rafts of epithelial cells have been implicated include without limitation: lung infections with influenza A and respiratory syncytial virus (RSV) (viruses which rely on epithelial lipid rafts for their entry and/or exit from cells during their life cycle and therefore would be susceptible to EMP2 function) and certain cell-invasive bacteria that infect the lung, for example, *Legionella pneumophila*, Mycobacteria, and *Pseudomonas aeruginosa* (bacteria which enter cells via lipid rafts and/or caveolae and therefore would be susceptible to EMP2 function).

In some embodiments, the lung disorder may be a TGF-β mediated lung disorder. Examples include without limitation, pulmonary fibrosis and acute lung injury. In some embodiments, the lung disorder may comprise an epithelium-matrix interaction. Examples include without limitation, idiopathic pulmonary fibrosis.

EMP2 is implicated in the injury, as well as the repair phase of phase of acute and chronic lung diseases. In some embodiments, the lung disorder may be an acute disease, such as acute lung injury, acute respiratory distress syndrome, pneumonia, viral infection, and airway hyperresponsiveness. In some embodiments, the lung disorder may be a chronic disease, such as COPD, bronchiectasis, radiation- or chemotherapeutic-induced pneumonitis, idiopathic or induced interstitial lung disease, bronchopulmonary dysplasia, and lung fibrosis. Induced interstitial lung disease may be induced by a drug, an autoimmune disease, an occupational hazardous agent or an environmental pollutant. In some embodiments, the lung disorder may be due to exposure to a toxic agent, such as a bioterroristic agent, an occupational hazardous agent or an environmental pollutant. Examples include without limitation, chlorine, hydrogen sulfide, mustard gas. In some embodiments, the lung disorder may be chemical pneumonitis due to aspiration of a chemical, acid or hydrocarbon or due to smoke inhalation.

In some embodiments, the agent or a composition comprising the agent is administered to an infant at risk for acute lung injury due to meconium aspiration or prematurity.

In another aspect, the present invention includes a method to detect alveolar epithelial type 1 cell injury in lung disease in a subject by measuring the level of EMP2 in a sample obtained from the subject. The level of EMP2 may be measured by measuring the level of EMP2 protein or the level of mRNA encoding EMP2. Methods for measuring these are known in the art. Any suitable sample may be used. Examples include without limitation, plasma, serum or bronchoalveolar lavage fluid.

In another aspect, the present invention includes a method to target a molecule to alveolar epithelial type 1 cells comprising co-administering the molecule with an agent that binds EMP2. The term "subject" refers to any mammal. In some embodiments, the subject is a human.

In another aspect, the present invention includes kits containing a composition comprising the agent in a unit dosage form. The kit may be a therapeutic kit for the treatment or prevention of a lung disorder, or a diagnostic kit for the detection or monitoring of alveolar epithelial type 1 cell injury in a lung disease. The kit may include a sterile container which contains the composition; such containers can be boxes, ampoules, bottles, vials, tubes, bags, pouches, inhalers, nebulizers or other suitable container forms known in the art. Such containers can be made of plastic, glass, laminated paper, metal foil, or other materials suitable for holding medicaments.

A therapeutic kit may include instructions for administering the agent to a subject having or at risk of developing a lung disease. A diagnostic kit may include instructions for using the agent for diagnostic purposes. The instructions will generally include information about the use of the composition for the treatment or prevention of the lung disease, or for diagnostic purposes. The instructions may include at least one of the following: description of the agent; dosage schedule and administration for treatment or prevention of the disease or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

The practice of the present invention may employ conventional techniques of molecular biology (including recombinant techniques), microbiology, cell biology, biochemistry, nucleic acid chemistry, and immunology, which are well known to those skilled in the art. Such techniques are explained fully in the literature, such as, Methods of Enzymology, Vol. 194, Guthrie et al., eds., Cold Spring Harbor Laboratory Press (1990); Biology and activities of yeasts, Skinner, et al., eds., Academic Press (1980); Methods in yeast genetics: a laboratory course manual, Rose et al., Cold Spring Harbor Laboratory Press (1990); The Yeast *Saccharomyces*: Cell Cycle and Cell Biology, Pringle et al., eds., Cold Spring Harbor Laboratory Press (1997); The Yeast *Saccharomyces*: Gene Expression, Jones et al., eds., Cold Spring Harbor Laboratory Press (1993); The Yeast *Saccharomyces*: Genome Dynamics, Protein Synthesis, and Energetics, Broach et al., eds., Cold Spring Harbor Laboratory Press (1992); Molecular Cloning: A Laboratory Manual, second edition (Sambrook et al., 1989) and Molecular Cloning: A Laboratory Manual, third edition (Sambrook and Russel, 2001), (jointly referred to herein as "Sambrook"); Current Protocols in Molecular Biology (F. M. Ausubel et al., eds., 1987, including supplements through 2001); PCR: The Polymerase Chain Reaction, (Mullis et al., eds., 1994); Harlow and Lane (1988) Antibodies, A Laboratory Manual, Cold Spring Harbor Publications, New York; Harlow and Lane (1999) Using Antibodies: A Laboratory Manual Cold Spring Harbor Laboratory Press, Cold Spring Harbor, N.Y. (jointly referred to herein as "Harlow and Lane"), Beaucage et al. eds., Current Protocols in Nucleic Acid Chemistry John Wiley & Sons, Inc., New York, 2000); Casarett and Doull's Toxicology The Basic Science of Poisons, C. Klaassen, ed., 6th edition (2001), and Vaccines, S. Plotkin and W. Orenstein, eds., 3rd edition (1999).

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

The following examples are provided for the purpose of illustration and are not intended to limit the scope of the present invention. Each publication, sequence or other reference disclosed below and elsewhere herein is incorporated herein by reference in its entirety, to the extent that there is no inconsistency with the present disclosure.

EXAMPLES

The following materials and methods were used in the examples.

Mice. Emp2−/− mice have been described (29) and were on a C57BL/6 background. Age- and gender-matched WT littermate controls were used. In a subset of experiments C57BL/6 controls were used (Jackson Laboratory, Bar Harbor, Me.). SftpcCreERT2+/−; Rosa26-mTmG+/− mice were treated with tamoxifen and euthanized at age 9-10 wk, as previously described (30, 31). All experiments were performed in accordance with the Animal Welfare Act and the U.S. Public Health Service Policy on Humane Care and Use of Laboratory Animals after review by the NIEHS Animal Care and Use Committee.

Mouse exposures and harvests. Mice were administered 150-2000 CFU *K. pneumoniae* (ATCC 43816), 2×105 CFU *S. pneumoniae* (serotype 3, ATCC 6303), or 1×106 CFU *P. aeruginosa* (PAO1, ATCC HER-1018), or 0.5 µg CXCL1 (R&D Systems) by oropharyngeal aspiration while under flow-regulated isoflurane anesthesia. For microbiological analysis, lung was homogenized in 1×PBS, and serial dilutions plated on blood agar for bacterial quantification. Splenic homogenate and whole blood were serially diluted and plated on tryptic soy agar (TSA) plates. In other studies, mice were exposed to aerosolized *Escherichia coli* 0111:B4 LPS (300 µg/mL, Sigma-Aldrich, St. Louis, Mo.) for 30 min, as previously reported (4). For airspace analysis, BALF was spun at 300×g for 6 min. Cells were then resuspended in PBS and counted. Cytospins were stained and differentials counted by light microscopy. In order to evaluate peritoneal trafficking of PMNs, mice were injected i.p. with 0.5 µg CXCL1, and sacrificed 4 h later for peritoneal lavage.

Generation of bone marrow chimeric mice. Procedures were followed as previously described (32). Emp2+/+ mice that were congenic for CD45 (stock no. 002014; Jackson Laboratory) were used. Recipients were lethally irradiated (900 rad) by a Model 431 irradiator using a 137Cs source (JL Shepherd and Associates, San Fernando, Calif.). Within 4 hours after irradiation, donor-derived bone marrow from femurs and tibias (2×106 cells) was injected i.v. into recipients. The efficiency of donor stem cell engraftment was determined by flow cytometry for CD45.1 (Emp2+/+) 9 weeks after transfer on circulating PMNs (Gr-1+) and B lymphocytes (B220+). Engraftment efficiency within all experimental animals was greater than 90%. Chimeras were used a minimum of 12 weeks post-transplant.

Flow cytometry and fluorescence-activated cell sorting. Lung tissues were perfused, digested, and processed to single cell suspension as previously reported (33). Cells were blocked with anti-mouse CD16/32 and stained for 30 min with antibodies against: CD47 (miap301), ICAM-1 (3E2) and Integrin beta 3 (HMβ3-1). In some studies, cells were stained with 1 µg/ml cholera-toxin B-Alexa Fluor 488 (Thermo Fisher Scientific) to stain lipid rafts, as previously described (34). All flow cytometry analyses were performed on the LSR II (BD Biosciences) and analyzed using FACS-Diva (BD) and FlowJo software (Tree Star). For cell sorting, lungs were perfused, inflated, and digested with elastase (Worthington Biochemicals, Lakewood, N.J.) for 45 min at 37° C. Minced lung was then digested with DNase (Sigma, St. Louis, Mo.) for 15 min. Cells were strained (70 µm filter), depleted of CD45+ cells using AutoMACS column (Miltenyi Biotec, San Diego, Calif.), and then blocked with anti-mouse CD16/CD32 (2.4G2) and normal mouse and rat serum (Jackson ImmunoResearch, West Grove, Pa.). Cells were incubated with one or more of the following antibodies/markers: CD34 (MEC14.7), CD45 (104), EpCAM/ CD326 (G8.8), CD31 (390), T1 □/podoplanin (8.1.1), as well as LysoTracker® (Thermo Fisher Scientific) and 7-AAD (Biolegend, San Diego, Calif.). AT1 (7-AAD-CD31- CD34-CD45-EpCAM+T1α+Lyso−) and AT2 (7-AAD− CD31−CD34−CD45−EpCAM+T1α−Lyso+) cells were then sorted on an ARIA-II flow cytometer (BD Biosciences) with purity >92-97%. In some experiments, AT2 cells were alternatively identified for sorting by GFP-positivity, with the use of SPC-GFP transgenic mice. In some experiments, CD45−EpCAM+ cells were grown in tissue culture plates for up to 14 days to induce AT1-like cells, as previously reported (35). Rat alveolar epithelial cells were purified from lung as previously reported (36) and cultured over multiple days.

Quantitation of pulmonary interstitial PMNs. A reported procedure was followed with minor modifications (37). In brief, LPS-exposed mice were injected i.v. with 10 μg HTC-conjugated anti-CD45 (clone 30-F11) 5 minutes prior to sacrifice. Euthanized mice were exsanguinated via cardiac puncture, and then underwent BAL with ~2-3 mL 1×PBS and pulmonary vascular perfusion with ~10 mL 1×PBS. Lavaged and perfused lungs were excised and minced in the presence of 100 μg/mL unlabeled anti-CD45 (clone 30-F11) and digested in a cocktail of liberase/DNase/collagenase XI/hyaluronidase (60 min, 37° C.), followed by passage through a cell strainer. After erythrocyte lysis, cells were centrifuged (1600 rpm, 5 min), blocked (5% normal mouse serum, 5% normal rat serum, and 5 ug/ml [1:100] Fc blocker in FACS buffer), stained with APC-conjugated anti-Ly6G (clone 1A8), and resuspended for flow cytometry. Endovascular PMNs were identified as CD45+Ly6G+ and interstitial (extravascular) PMNs as CD45−Ly6G+. In pilot studies, we confirmed that no intravitally-labelled (CD45+) PMNs were detectable in BALF.

Live lung slice imaging. Lungs (N=3-4 mice/genotype) were harvested, cultured, stained, and imaged as previously described (38).

Immunofluorescence studies of fixed lung tissue. Lung tissue was fixed, embedded in paraffin, sectioned, and immunostained for GFP (abcam #ab13970), EMP2 (rabbit serum, a kind gift from Dr. Madhuri Wadehra), SPC (Santa Cruz sc-7706), T1α (University of Iowa Developmental Studies Hybridoma Bank #8.1.1), CCSP (39), and acetylated tubulin (Sigma T7451), as previously described (31). Images were captured on a Leica SP5 confocal or a Zeiss Axioplan 2.0 microscope.

Clinical blood assays. Blood cell counts were analyzed using the HEMAVET 1700 hematology analyzer (Drew Scientific, Inc.). Manual leukocyte differential counts were performed, and smear estimates were used to confirm values.

Quantitative RT-PCR. Total RNA was extracted from cells and tissues with RNeasy kits (Qiagen) using the manufacturer's protocol. For tissue-extracted RNA, tissues were homogenized with a TissueLyser (Qiagen). For sorted lung epithelial cells or cultured primary AT1-like cells, the RNAqueous-Micro Total RNA Isolation kit (Thermo Fisher Scientific) was used with elution in a 20 al volume. Generally, 100-1000 ng RNA was converted to cDNA and used to perform qPCR reactions on Applied Biosystems™ ViiA™ 7 in duplicate. Pre-developed, validated primer/probe sets (Applied Biosystems) were used. The efficiency (slopes) of the target amplification and the efficiency of the reference endogenous control (GAPDH) amplification were 100% (±10%).

Cell lines and generation of stable cells. Cell lines Calu-3, NC 41292 were purchased from ATCC, and Let1 cells were a gift from Dr. Paul Thomas at St. Jude Hospital (40). For stable knockdown of EMP2 in Calu-3 and NCI-H292, lentiviral-based pLKO sectors that carry scrambled or EMP2-targeted shRNA were purchased from Sigma-Aldrich to transduce both cell lines. Stable transduced cells were selected and maintained in medium containing 2 ug/ml puromycin (InvivoGen). Doxycycline-inducible Cav2 knockdown cells were generated in the EMP2 knockdown Calu-3 stable line by transduction of a lentiviral vector EZ-Tet-pLKO-Blast (Addgene, (41) that express caveolin 2 shRNA targeting sequence (TRCN0000123019; TRCN0000123022; TRCN0000296146). To express EMP2 wildtype or mutants in Let1 cells, EMP2 cDNA was purchased, and point mutations were introduced to CRAC or CARC sites in EMP2 DNA sequence and then cloned into lentiviral vector pLV-EF1a-IRES-Puro (Addgene). Let1 cells were transduced by established lentiviral constructs with puromycin selection at a concentration of 2 ug/ml.

In vitro studies of neutrophil transepithelial migration. Collection of PMNs from normal, healthy donors was in accordance with an NIEHS institutional review board-approved protocol. Procedures were followed as previously reported, with minor modifications (42). Briefly, Calu-3 cells (0.55×106/well) (42) or Let1 cells (0.4×106/well) were seeded on the undersurface of polycarbonate membranes in Transwell tissue culture inserts (Corning) and then grown to confluence (transepithelial resistance ≥1,000 Ω·cm2). Three million human neutrophils, freshly isolated by discontinuous plasma-Percoll gradient centrifugation (43), were added to the upper chamber, and 0.5 nM fMLP (Sigma-Aldrich) was added to the lower chamber. Transmigration was allowed to proceed for 30-150 min, after which PMNs were quantified in the lower chamber with a quantitative myeloperoxidase assay (44).

Fluorescence microscopy. Cultured cells were stained with cholera toxin B and imaged by microscopy as previously reported (45).

Cytokine analysis. Cytokines were quantified by multiplex assay (Bio-Plea; Bio-Rad Laboratories) or ELISA (eBioscience).

BCA protein assay. Manufacturer's instructions (Pierce) were followed, with colorimetric reading at OD562 on a Bio-Tek Synergy 2 microplate reader.

Immunoblotting. For detection of EMP2 protein, cell lysates were treated with PNGase (New England Biolabs; 60 min, 37° C.) as previously reported (29). Equal protein mass from cell lysates was run on a 10% sodium dodecyl sulfate-polyacrylamide gel and transferred to a PVDF membrane using standard methods. The membrane was probed with rabbit anti-EMP2 (1:1000) and rabbit anti-β-actin (1:1000; Cell Signaling Technology, Danvers, Mass.). Membranes were then washed and exposed (60 min) to 1:5000 HRP-conjugated secondary antibody (GE Healthcare) in 5% milk/buffer. After further washes, signal was detected with ECL Western Blot detection reagents (GE Healthcare), followed by film exposure (GE Healthcare).

Histopathologic analysis. Tissues were fixed in 10% neutral buffered formalin, trimmed, processed for paraffin, embedding, sectioned (5 μm), and stained with H&E. The slides were scanned using an Aperio slide scanner (Leica Biosystems, IL) and images were captured using Aperio's ImageScope.

Example 1

This example illustrates the expression pattern of EMP2 in various airway epithelial cells and cell lines.

Figure 6A:
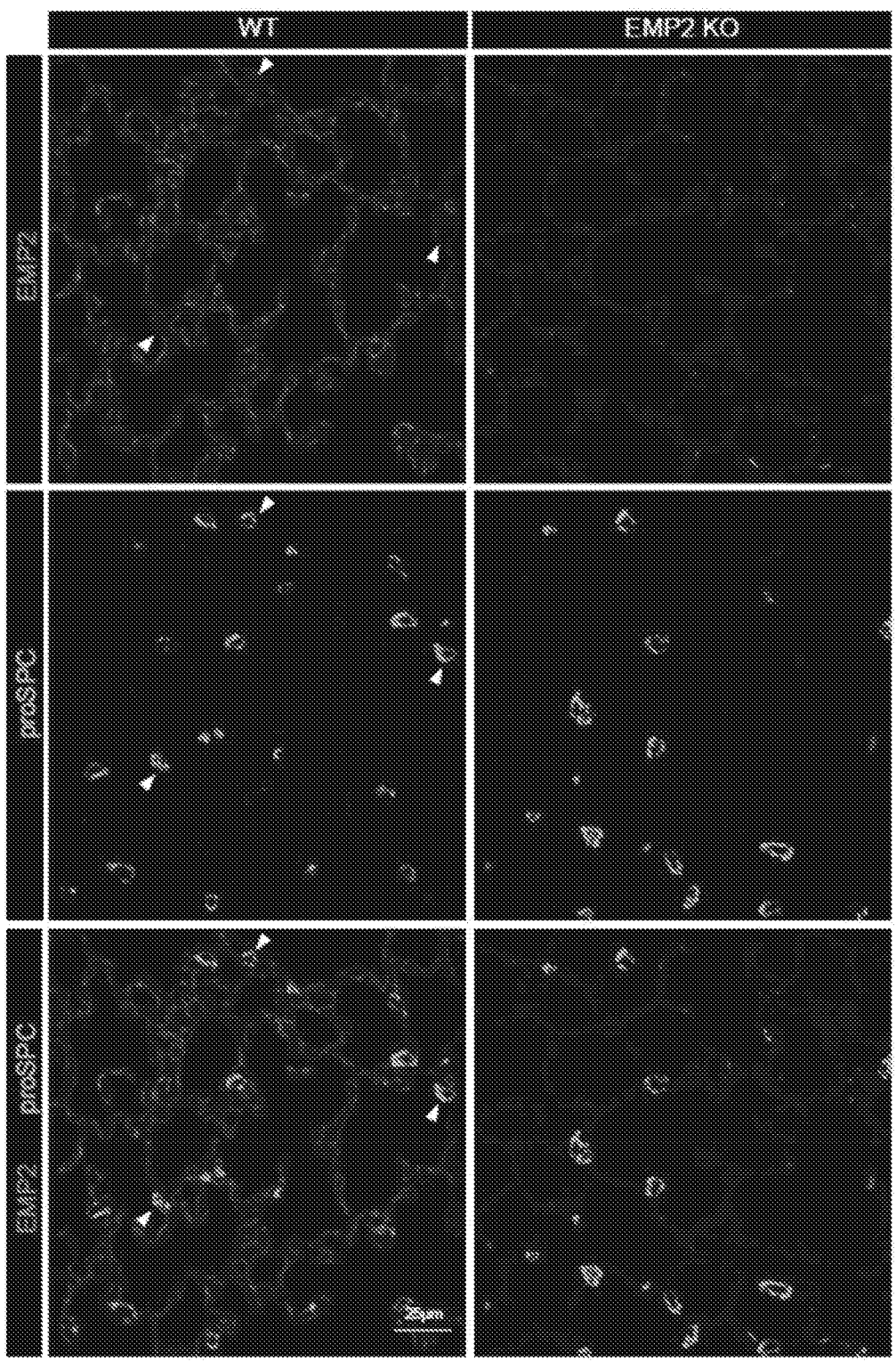
FIGS. 6A-6C show that EMP2 is expressed in AT1 but not AT2, Club, or ciliated cells. (A) Lung sections from Emp2+/+ and Emp2−/− mice were immunostained for EMP2 and surfactant protein C (SPC). Arrowheads indicate ATII cells. (B) Lung sections from SftpcCreERT2+/−; Rosa26-mTmG+/− mice were stained for EMP2, GFP, and T1α. Open arrowheads indicate AT1 cells. Closed arrowheads indicate points at which AT2 cells comprise the apical epithelial surface, as indicated by expression of GFP with gaps in T1α and EMP2 staining. (C) Lung sections from Emp2+/+ and Emp2−/− mice were immunostained for EMP2, Club cell secretory protein (CCSP, a Club cell marker), and acetylated tubulin (a ciliated cell marker). Arrowheads indicate nonspecific staining with the EMP2 antibody, which is seen in both Emp2+/+ and Emp2−/− mice airways. Images were taken at 40-63× magnification and are representative of n≥3 mice.
Figure 6B:
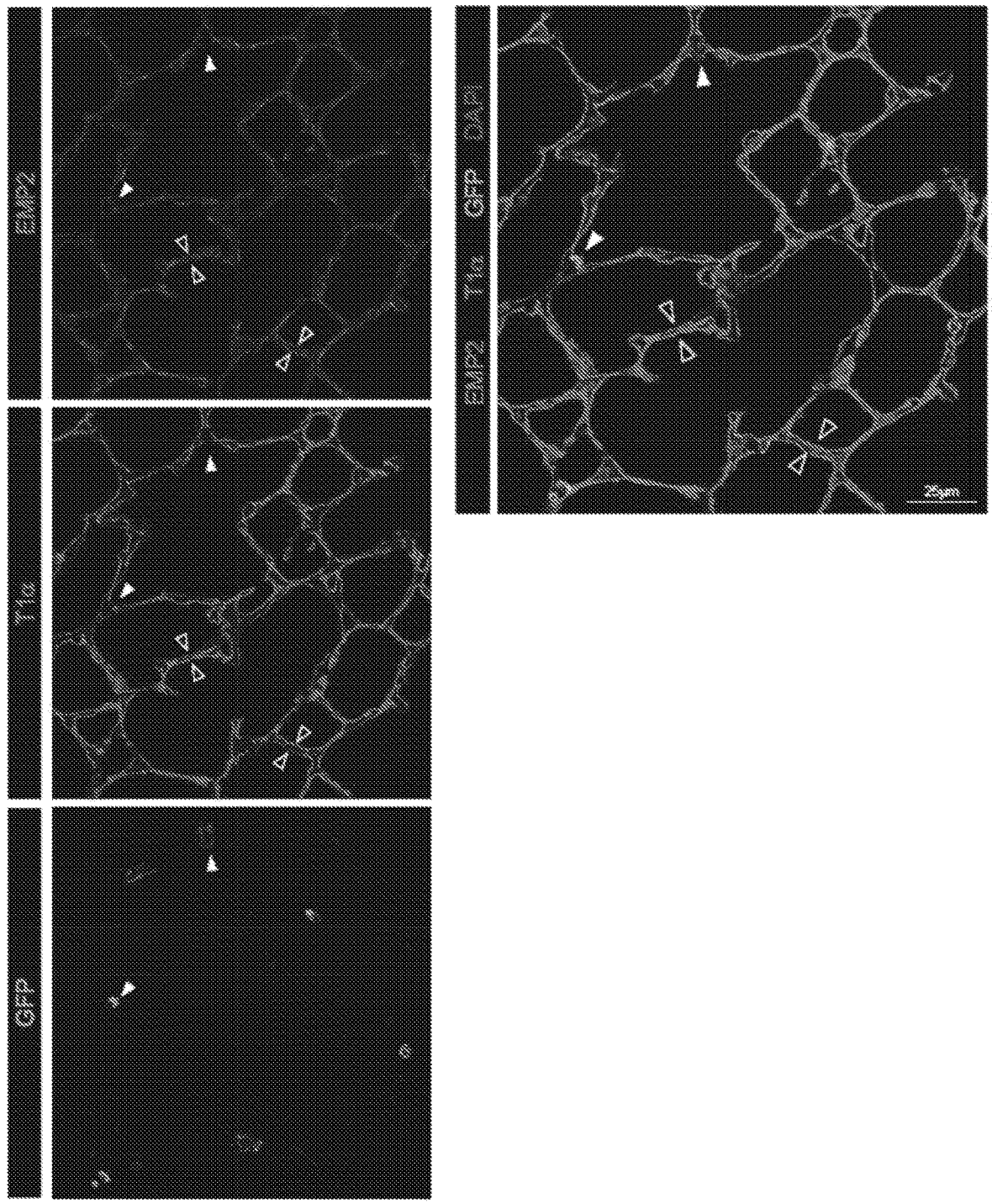
Figure 6C:
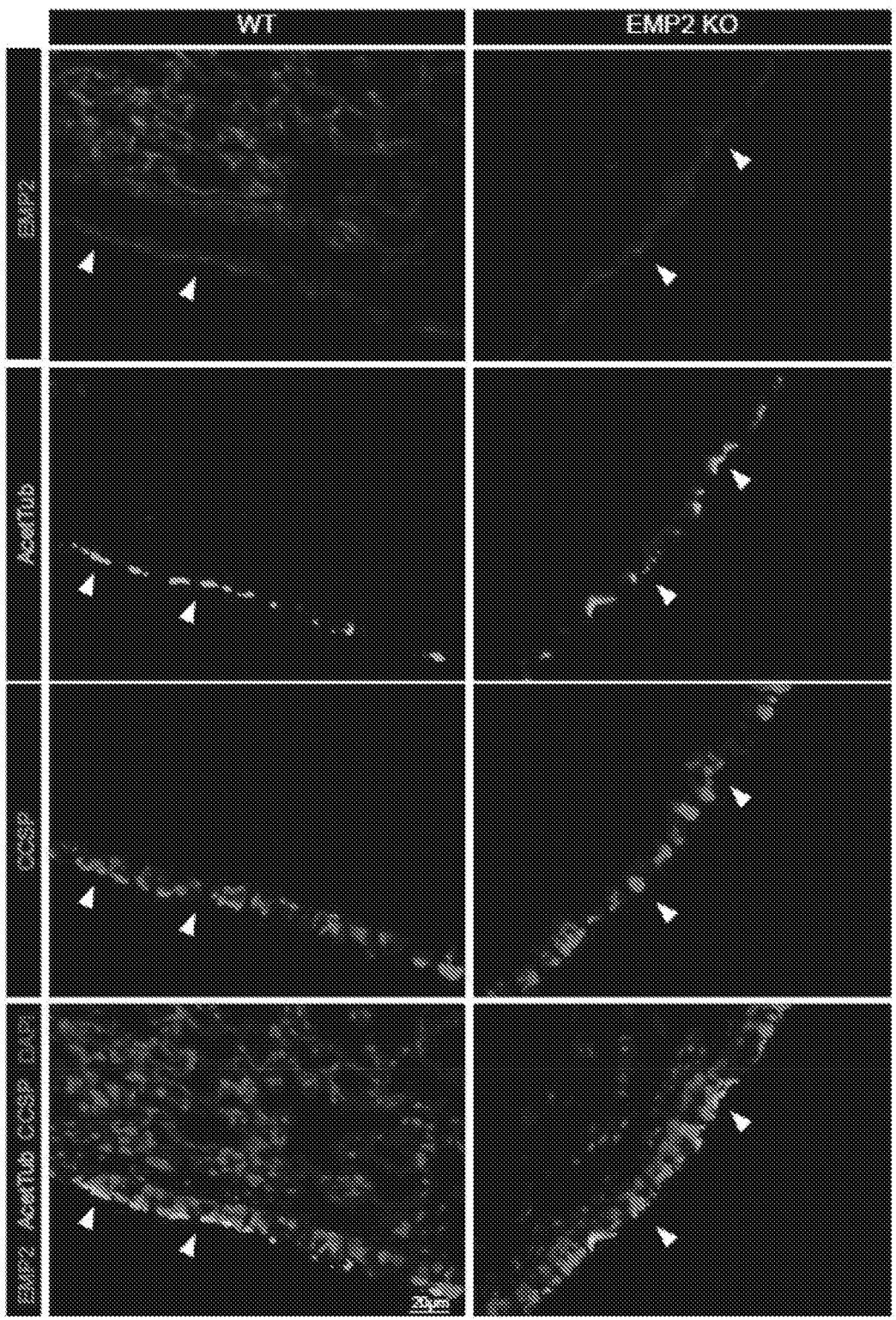
Figure 7A:
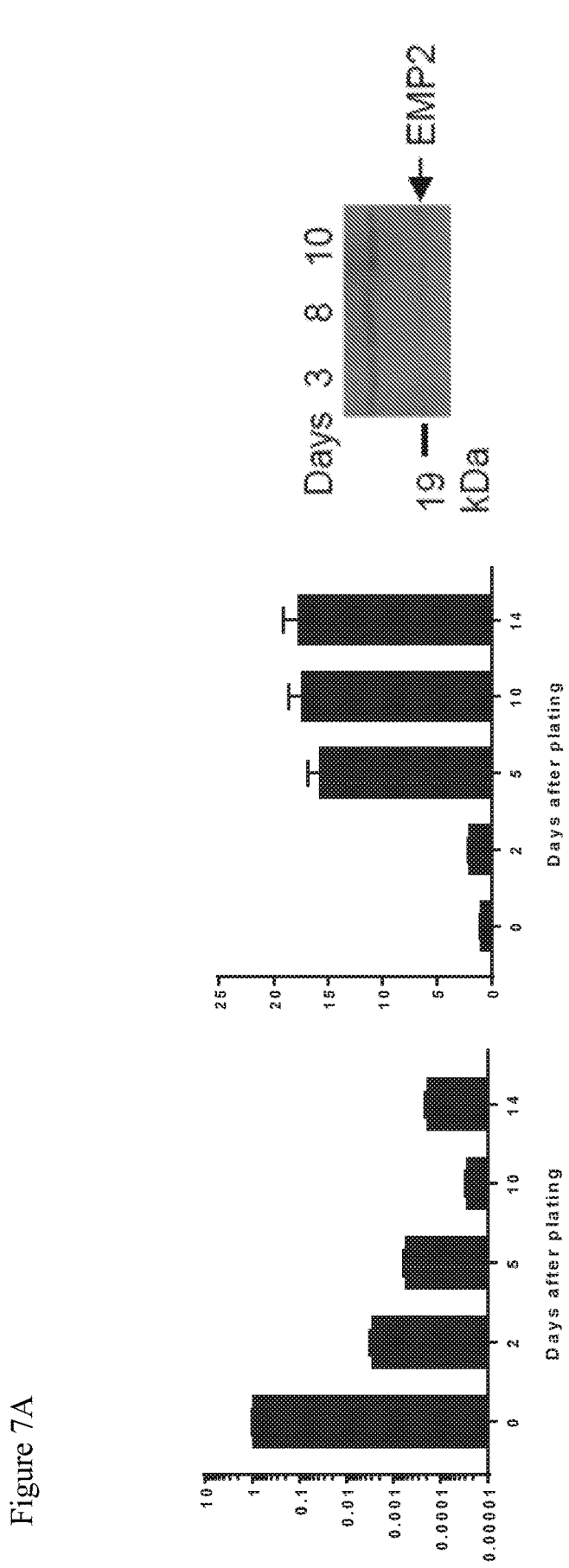
FIGS. 7A-7C show the expression of EMP2 protein in lung epithelial cells. (A) Epithelial cells were purified from WT mouse lung and then cultured for 14 days to induce an AT1-like cell phenotype. On the various culture days shown, surfactant protein C (SP-C, an AT2 marker) and podoplanin (AT1 marker) mRNA were quantified by RT-qPCR (mean±SEM) and EMP2 protein was detected by immunoblot. (B) Rat lung AT2 cells were purified and cultured over a time course as shown (duplicate wells). At the various durations of culture shown, EMP2 was immunoblotted. (C) Cell lysates from Beas-2B, Calu-3, and H292 cells were immunoblotted for EMP2 and actin (loading control) before and after treatment with PNGase to remove glycosylation, yielding EMP2 at its expected 19 kDa molecular weight. Data are representative of at least 3 independent experiments.
Figure 7B:
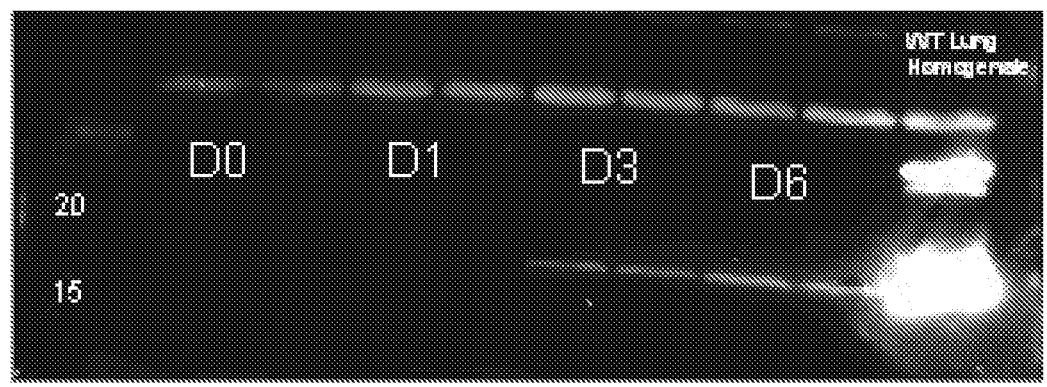

EMP2, a tetraspan membrane protein, is reportedly expressed in AT1, but not AT2 cells nor AMs in rat and human lung (12). EMP2 transcripts were readily detected in AT1, AT2, and airway epithelial cells sorted from murine lung (FIGS. 5A-5E), but specific signal for EMP2 protein was observed only in AT1 cells (FIGS. 6A-6C), indicating post-transcriptional regulation. Further, EMP2 protein was induced in a time-dependent fashion in both mouse and rat primary AT2 cells during in vitro transdifferentiation into AT1-like cells (FIGS. 7A-7B).

Figure 7C:
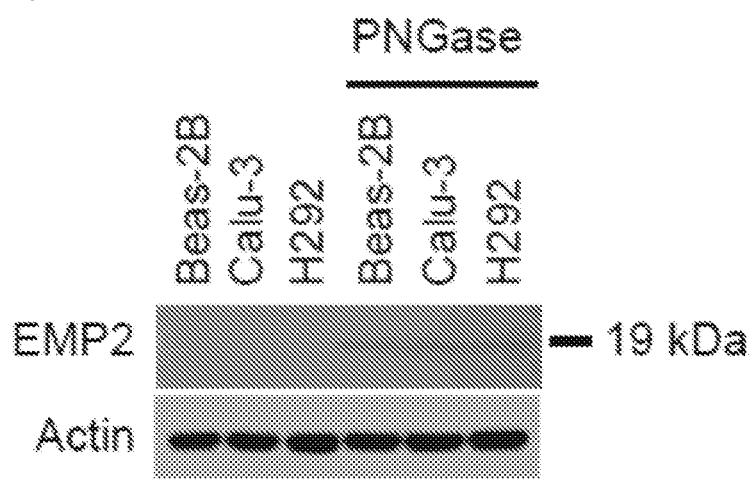

Surveying a panel of pulmonary epithelial cell lines, it was found that surprisingly EMP2 protein was readily detectable in several airway lines (Calu-3, Beas-2B, H292) (FIG. 7C), but undetectable in three AT1-like cell lines (E10, Let1, R3/1).

Example 2

This example illustrates that EMP2 regulates transepithelial migration (TEM) of neutrophils into the alveolar lumen in response to diverse airway exposures.

Figure 8A:
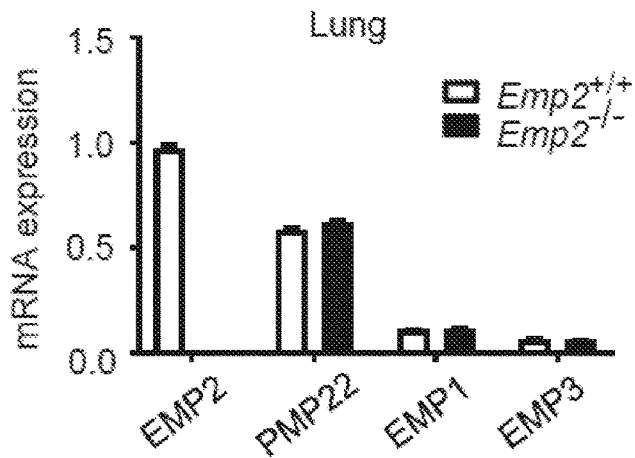
FIGS. 8A-8C show the normal basal phenotype of EMP2-null mice. (A) Emp2, Pmp22, Emp1, and Emp3 mRNA were quantified in lung homogenates from naïve Emp2+/+ and Emp2−/− mice. (B) Total leukocytes (WBCs), alveolar macrophages (AM), and neutrophils (PMNs) were quantified by morphology in bronchoalveolar lavage (BAL) of naïve Emp2+/+ and Emp2−/− mice (N=5/genotype). (C) Protein concentration was quantified in BAL fluid (BALF) from naïve Emp2+/+ and Emp2−/− mice (N=5/genotype). Data are the mean±SEM and are representative of at least 3 independent experiments.
Figure 8B:
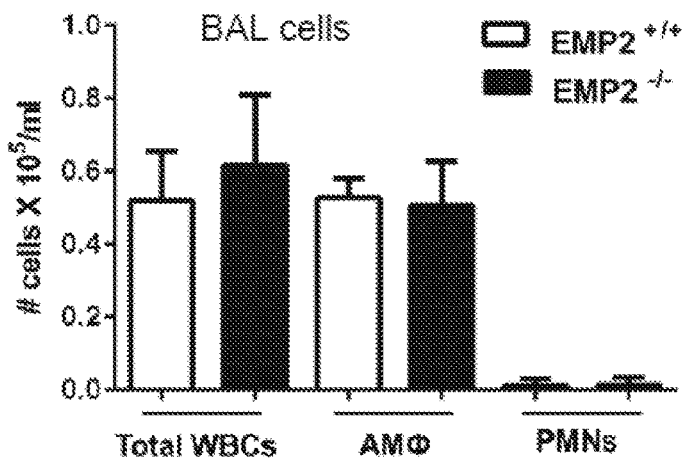
Figure 8C:
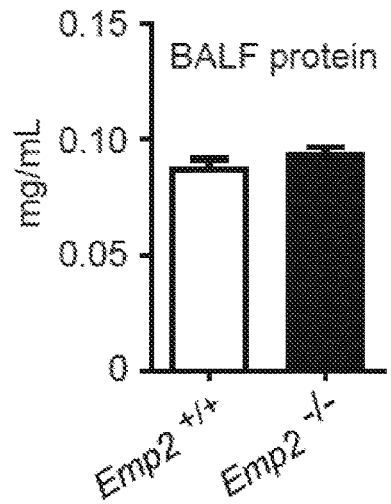

To test the role of EMP2 in pulmonary disease defense, Emp2-null mice were generated. Naïve Emp2−/− mice had no change in pulmonary expression of the alternate tetraspan family members Emp1, Emp3, and Pmp22, and no overt changes in lung histology, resident AM number, or bronchoalveolar lavage fluid (BALF) protein concentration (FIGS. 8A-8C).

Emp2+/+ and Emp2−/− mice received inhaled exposures to LPS, Gram-negative bacteria (*K. pneumoniae*, *P. aeruginosa*), and Gram-positive bacteria (*S. pneumoniae*) as shown FIGS. 1A-1D, and bronchoalveolar lavage (BAL) neutrophils (PMNs) were counted at various time points (A) or 24h post-exposure (B-D) (N=5-7/genotype). Upon the inhalational challenge, Emp2−/− mice exhibited a striking reduction in alveolar neutrophilia triggered by the inhalants (FIGS. 1A-1D), suggesting a wide-ranging deficit in host defense.

Figure 9A:
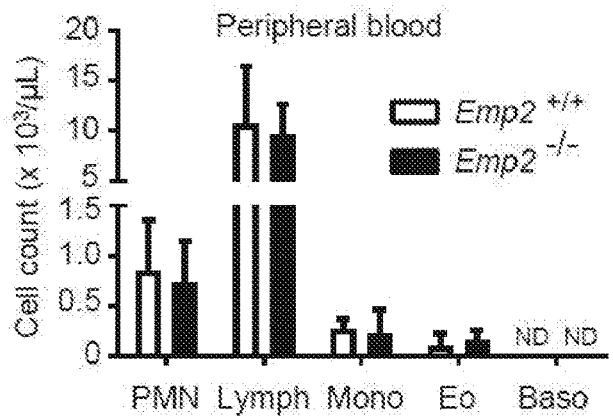
FIGS. 9A-9C show normal circulating leukocyte counts in EMP2-null mice. (A-C) Neutrophils (PMNs), lymphocytes (Lymph), monocytes (Mono), eosinophils (Eo), and basophils (Baso) were quantified in peripheral blood of Emp2+/+ and Emp2−/− mice in (A) the naïve state, (B) 24 h post-LPS inhalation, and (C) 24 h post-lung infection with K. pneumoniae (N=6/genotype). Data are the mean±SEM and are representative of at least 3 independent experiments. ND=not detected.
Figure 9B:
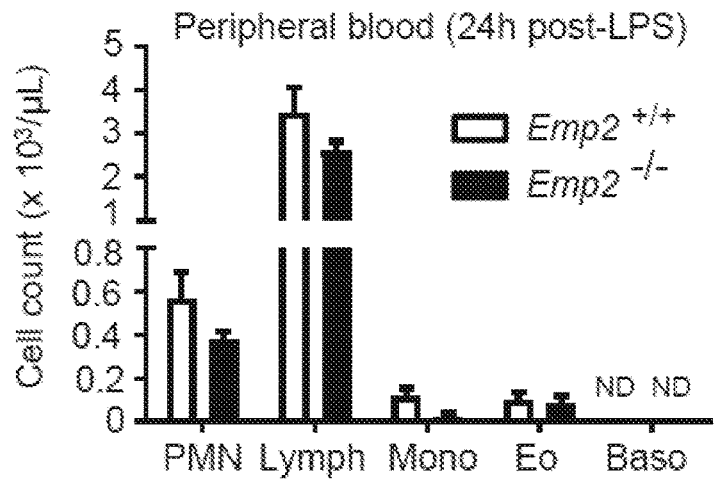
Figure 9C:
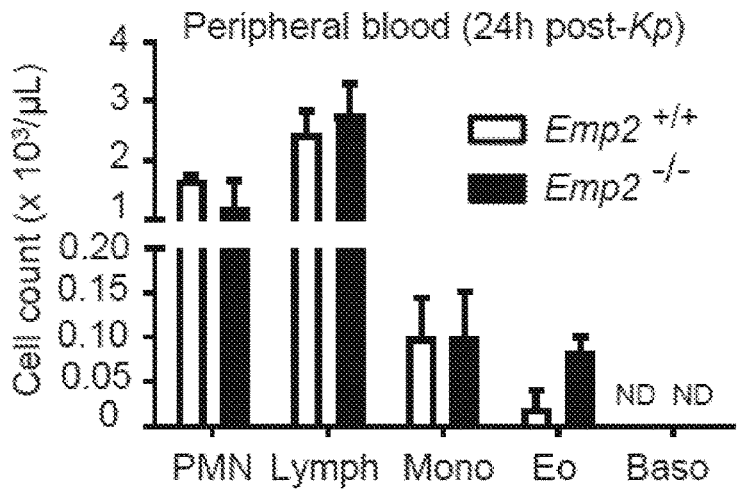

Given that TLR activation in AMs and AECs induces cytokines and chemokines that then attract circulating PMNs, it was initially predicted that Emp2−/− mice would have a reduction in these mediators in the airspace. However, BALF concentrations of cytokines and chemokines of established importance to PMN lung trafficking (3) were all normal 2h after LPS inhalation, a time point prior to substantial PMN influx (FIGS. 1A, 1E). Emp2+/+ and Emp2−/− mice also had equivalent numbers of circulating PMNs in the naïve, LPS-exposed, and *K. pneumoniae*-exposed state (FIGS. 9A-9C), suggesting no defect in supply of peripheral PMNs. Collectively, this suggested either a cell-intrinsic or -extrinsic deficit in migration of circulating PMNs to the airspace.

In support of deficient PMN trafficking, reduced influx of PMNs to the airspace was also observed after direct intratracheal (i.t.) inoculation of naive Emp2−/− mice with the chemokine CXCL1 (FIG. 1F). No differential secondary induction of CXCL5, reportedly produced by AT1 cells under some conditions (14), was observed in the airspace of CXCL1-inoculated Emp2−/− mice, suggesting that the differential PMN trafficking was a primary response to alveolar CXCL1. Notably, i.p. injection of CXCL1 elicited equivalent PMN influx into the peritoneal cavities of Emp2+/+ and Emp2−/− mice, demonstrating intact intrinsic chemotactic function of Emp2−/− PMNs in vivo (FIG. 1G).

Figure 1L:
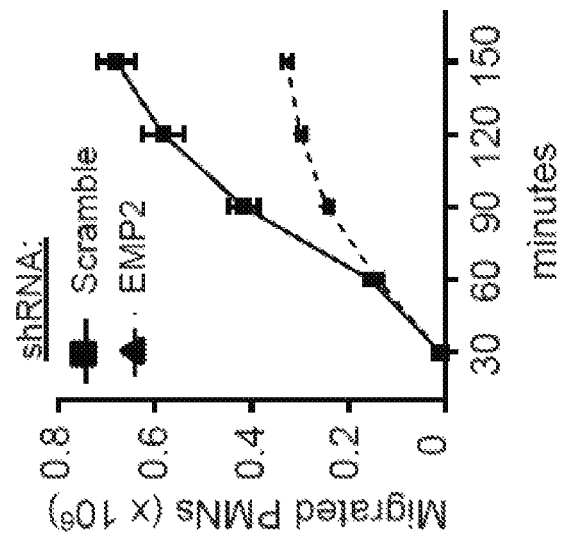
Figure 1K:
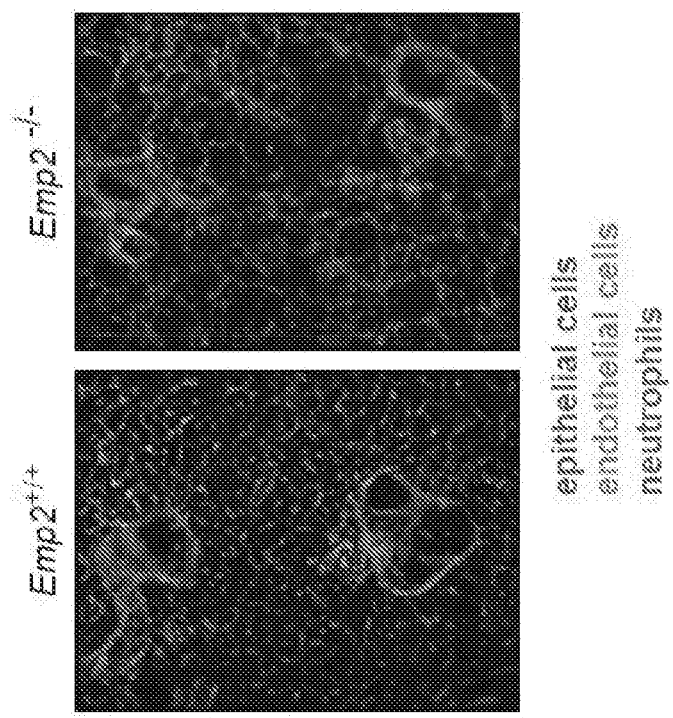

Chimeric mice made by bone marrow transfer revealed that EMP2 deletion in radioresistant lung cells, but not hematopoietic cells was sufficient to confer deficient alveolar PMN influx in response to inhaled LPS (FIG. 1H). This, in conjunction with the i.t. CXCL1 results, suggested that a defect in Emp2−/− AT1 cells causes deficient TEM of PMNs from the pulmonary interstitium into the alveolar lumen. Supporting this, a ~2-fold increase was found in PMNs in the parenchyma of perfused Emp2−/− lungs after LPS challenge (FIG. 1I). Intravital PMN labelling with i.v. antibody to distinguish endovascular from interstitial (extravascular) PMNs in perfused and airway-lavaged lungs confirmed a significant increase in interstitial PMNs in Emp2−/− mice following LPS (FIG. 1J), pointing to a deficit in PMN transit from interstitium to alveolus. This was further corroborated by live lung slice imaging, which revealed a marked increase in interstitial PMNs both in the peribronchoalveolar sheath surrounding, and in the wall of, small airways (FIG. 1K).

This result raises the possibility of an epithelial abnormality at the level of small airways in Emp2−/− mice. Given that multiple airway epithelial cell lines do express EMP2 (FIG. 7C), it is possible that EMP2 is expressed in the small airway epithelium in vivo but below the detection limit of the immunohistochemical antibody used. Alternatively, the distribution of interstitial PMNs in the Emp2−/− lung could conceivably arise from abnormal intra-tissue PMN trafficking that initiates from a primary defect at the level of the AT1 cell (e.g., necessitation up the bronchovascular sheath). A marked defect in migration of primary human PMNs in the physiological basolateral-to-apical direction through a monolayer of EMP2-silenced Calu-3 cells in response to fMLP was observed, suggesting that epithelial EMP2 deficiency is sufficient to attenuate PMN TEM. (FIG. 1L).

These data show that EMP2 deficiency leads to reduced transepithelial migration (TEM) of circulating neutrophils into the alveolar space in response to a variety of airway exposures such as LPS, Gram-negative bacteria (*K. pneumoniae*, *P. aeruginosa*), and Gram-positive bacteria (*S. pneumoniae*).

Example 3

This example illustrates that EMP2 deficiency dysregulates epithelial display of adhesion molecules.

Although there are robust examples of regulated PMN TEM into the alveolus (5), very few epithelial regulators of TEM have been specifically validated in the lung (4). Over 30 known β2 integrin ligands, plus multiple β1 integrin ligands are candidates (6). Studies deriving from intestinal epithelium have suggested that PMN β2 integrins initially engage fucosylated glycoprotein(s) on the basolateral epithelial surface, after which non-β2 integrin PMN proteins interact with CD47 and other epithelial proteins during paracellular transit (6). The β2 integrin ligand ICAM-1, although apically expressed in intestinal and alveolar epithelial cells, has been implicated in TEM at both sites, potentially by triggering cytoskeletal remodeling that facilitates paracellular passage of PMNs (15, 16). αvβ3 integrin, like ICAM-1 reportedly upregulated by EMP2 in cell lines (10), has also been implicated in LPS-induced alveolar neutrophilia (17), although a specific role for epithelial αvβ3 remains to be demonstrated.

As *S. pneumoniae*- and CXCL1-induced alveolar neutrophilia are fully, and LPS-induced neutrophilia, partially, CD18-independent (3, 18), it was initially reasoned that dysregulation of CD18-independent ligands in Emp2−/− epithelium could explain our findings. However, given that LPS-induced alveolar neutrophilia is estimated to be only ~20% CD18-independent (3), the marked PMN reduction observed in LPS- and Gram-negative bacteria-exposed Emp2−/− lungs (FIGS. 1A-1C), suggested that dysregulation of ligands for both CD18 and other PMN proteins was likely present in Emp2−/− epithelium.

Figure 2A:
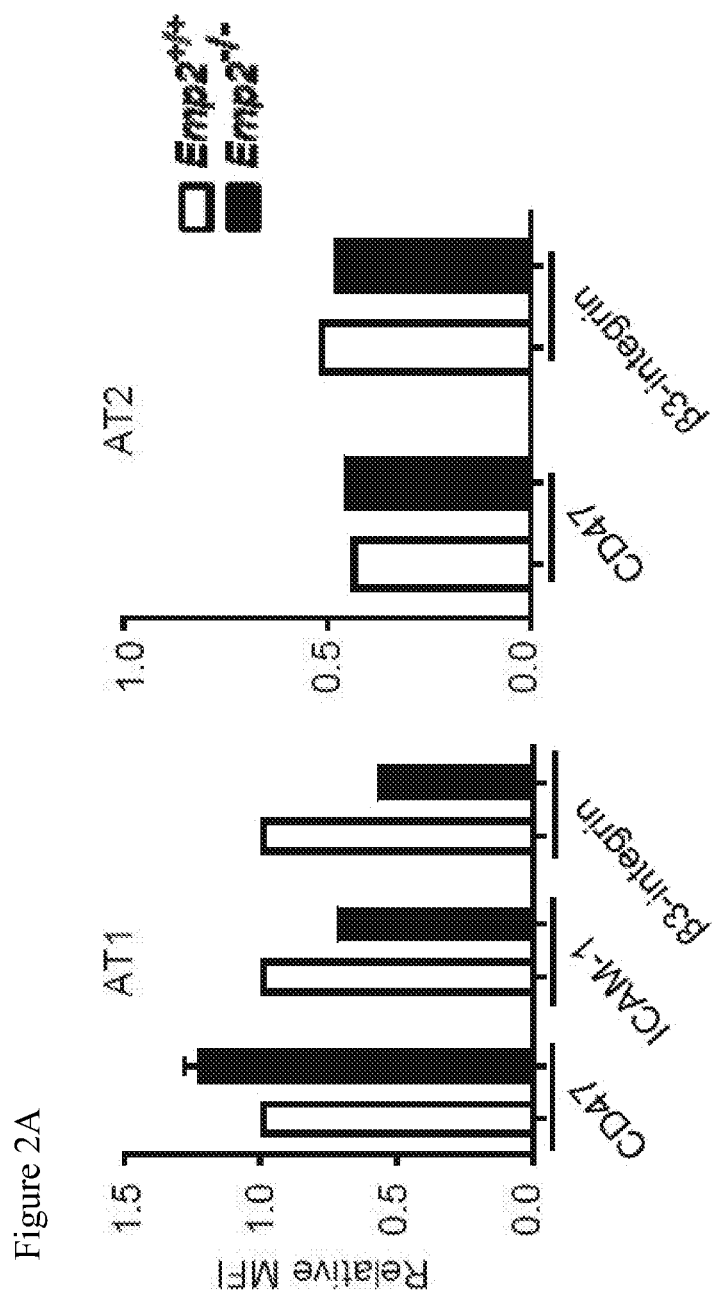
FIGS. 2A-2D illustrate that EMP2 deletion dysregulates epithelial surface display of adhesion molecules. (A) CD47, ICAM-1, and β3 integrin were quantified by flow cytometry on AT1 ($CD45^- CD31^- CD34^- EpCAM^+ T1\alpha^+ Lysotracker^-$) and AT2 ($CD45^- CD31^- CD34^- EpCAM^+ T1\alpha^+ Lysotracker^-$) cells from naïve $Emp2^{+/+}$ and $Emp2^{-/-}$ mice. (B-C) Calu-3 (B) and H292 (C) cells underwent lentiviral transduction with either scramble (Scr)- or EMP2-targeting shRNAs. EMP2 mRNA was quantified by qPCR, and surface CD47, ICAM-1, and β3 integrin were quantified by flow cytometry. (D) mRNA expression of EMP2, CD47, ICAM-1, and β3 integrin was quantified by qPCR in Calu-3 cells transduced as in panel B. Data are the mean±SEM and are representative of at least 3 independent experiments run with triplicate samples. *$P<0.05$, **$P<0.01$ by unpaired 2-tailed Student's test.
Figure 2B:
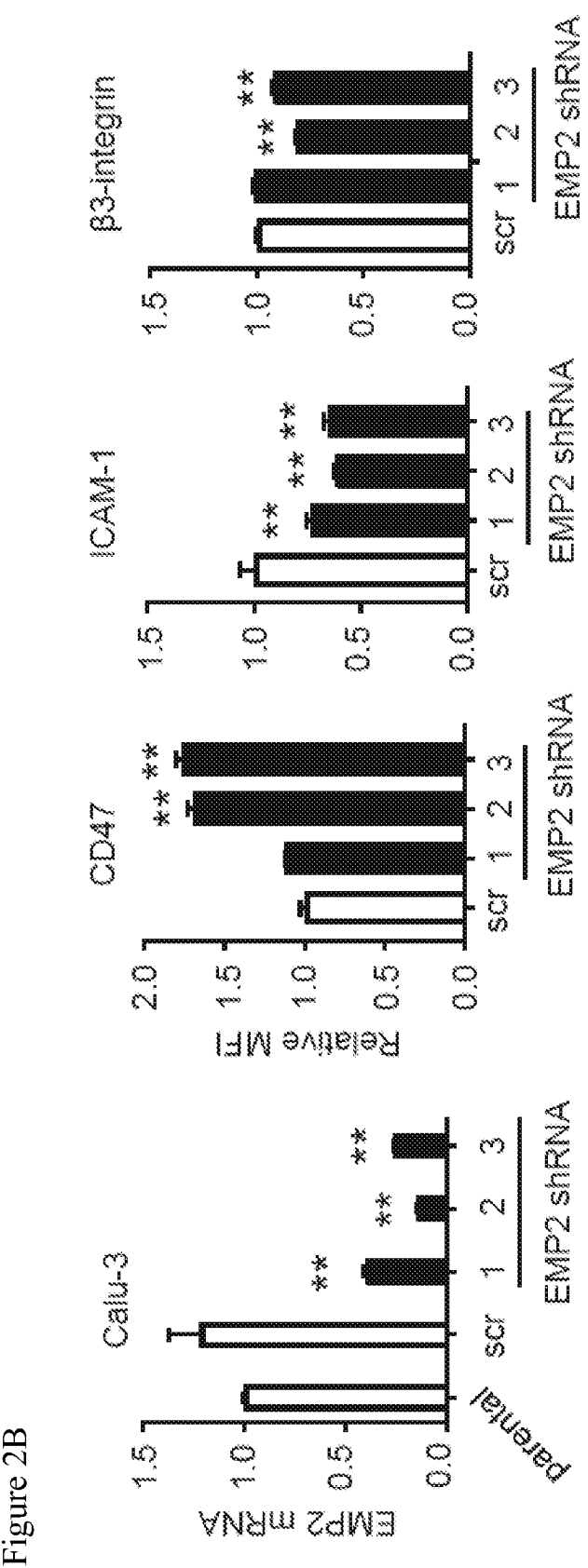
Figure 2C:
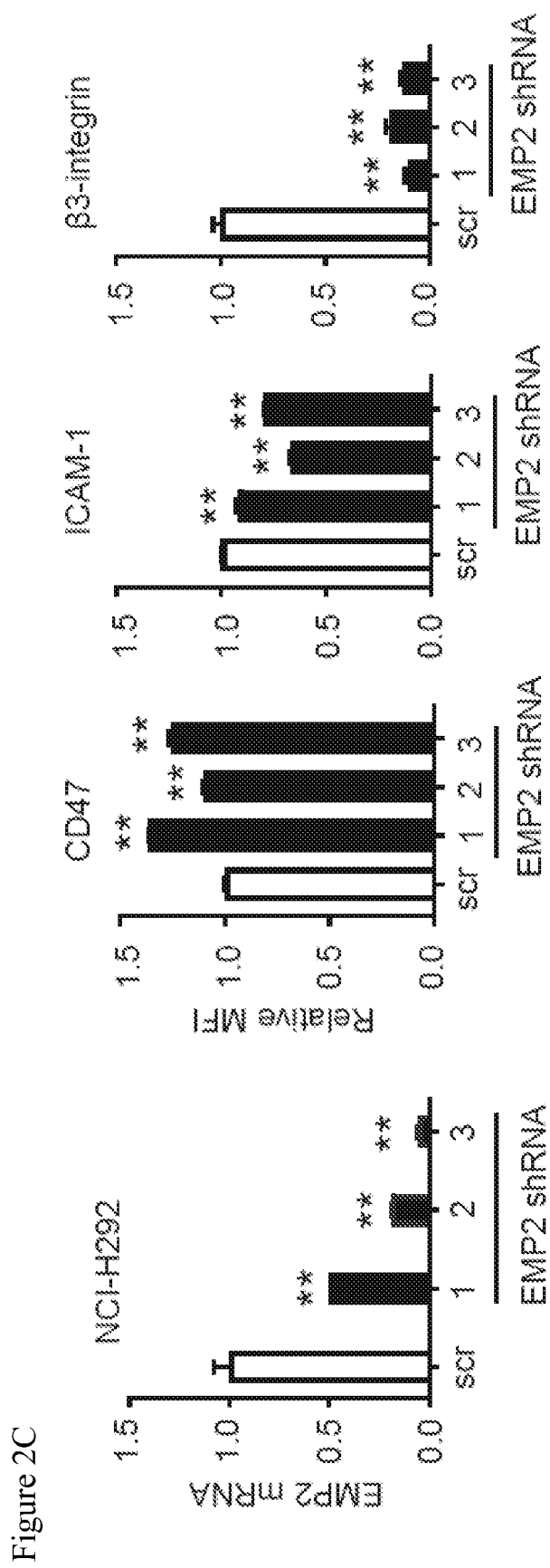
Figure 2D:
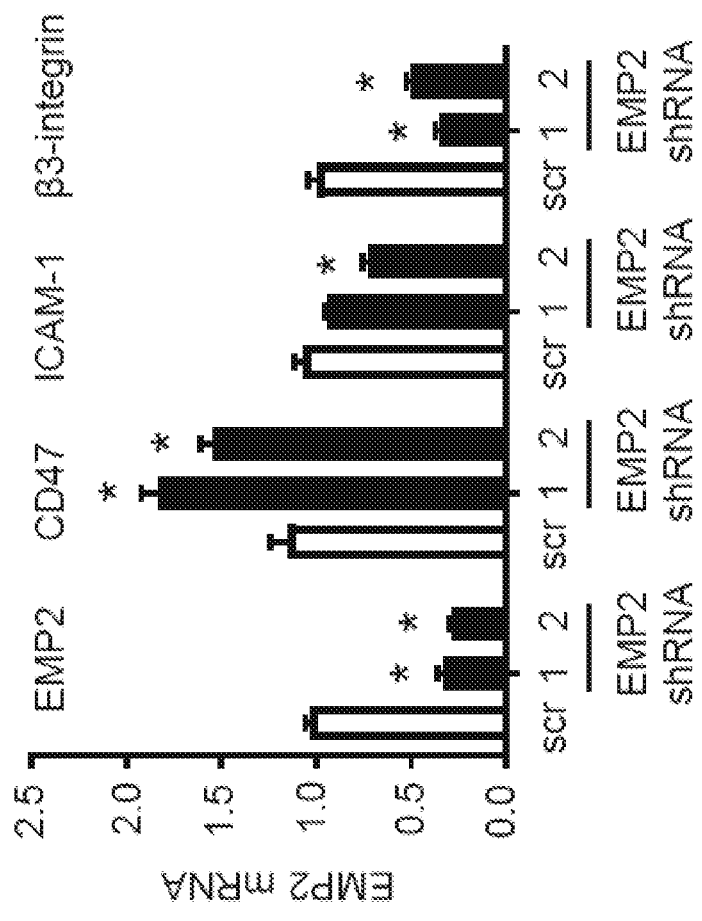
Figure 10:
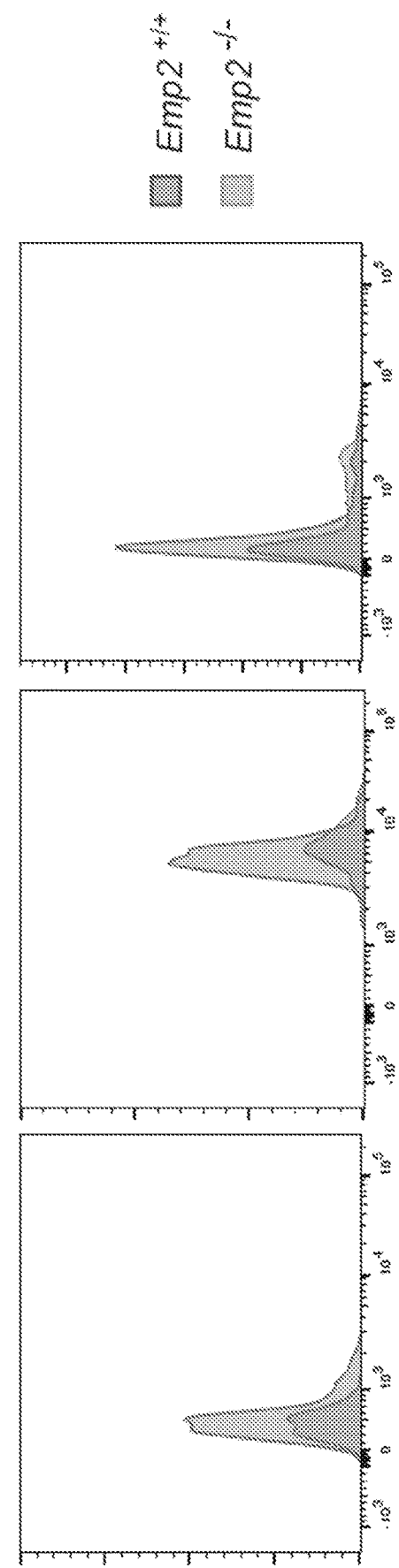
FIG. 10 shows representative flow cytometry histograms. AT1 cells (gating shown in FIG. 5D) from Emp2+/+ and Emp2−/− mice in the steady state were evaluated by flow cytometry for surface display of CD47, β3 integrin, and ICAM-1 as shown.

Using flow cytometry, it was found that surface display of CD47 was increased on AT1 (CD45−CD31−CD34−EpCAM+T1α+Lysotracker−) cells of Emp2−/− mice, whereas ICAM-1 and β3 integrin were reduced (FIG. 2A, FIG. 10), collectively indicating wide-ranging dysregulation of adhesion molecules on the AT1 plasma membrane. CD47 and β3 integrin were equivalent between Emp2+/+ and Emp2−/− AT2 (CD45−CD31−CD34−EpCAM+T1α-Lysotracker+) cells. EMP2 silencing in both Calu-3 cells and H292 cells largely recapitulated the adhesion molecule changes in in primary AT1 cells (FIGS. 2B-2C). It was further found that CD47 mRNA was upregulated and ICAM-1 and β3 integrin were downregulated in EMP2-silenced Calu-3 cells (FIG. 2D), suggesting that EMP2 may mediate membrane protein changes through transcriptional regulation.

These data show that EMP2 deficiency affects the expression of adhesion molecules on the epithelial plasma membrane through transcriptional regulation.

Example 4

This example illustrates that EMP2 is required for AT1 cell raft integrity.

Figure 3A:
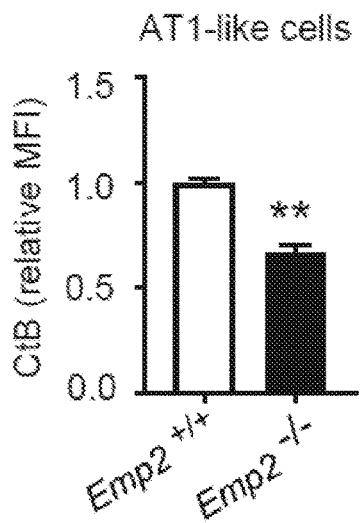
FIGS. 3A-3F show that EMP2 deletion depletes lipid rafts in epithelial cells. (A) Primary alveolar epithelial cells were purified from $Emp2^{+/+}$ and $Emp2^{-/-}$ lungs and cultured for 8 days to produce AT1-like cells. Lipid rafts were then quantified by flow cytometry of bound cholera toxin B (CtB)-AF488. (B-C) Calu-3 cells were transduced with scrambled (Scr)- or EMP2-targeting lentiviral shRNAs, after which CtB binding was quantified by flow cytometry (B) and by fluorescence microscopy (C). (D) H292 cells were transduced and analyzed for CtB binding as in panel B. (E) Let1 cells were transfected with EMP2 or empty vector. CtB binding by flow cytometry is shown at left, and relative EMP2 mRNA by qPCR at right. (F) Let1 cells were transfected with WT EMP2 or with EMP2 mutagenized in its CRAC or CARC sequences (see FIG. 11). Cells were then analyzed as in panel E. Data are the mean±SEM and are representative of at least 3 independent experiments. *$P<0.05$, **$P<0.01$ by unpaired 2-tailed Student's test.
Figure 3B:
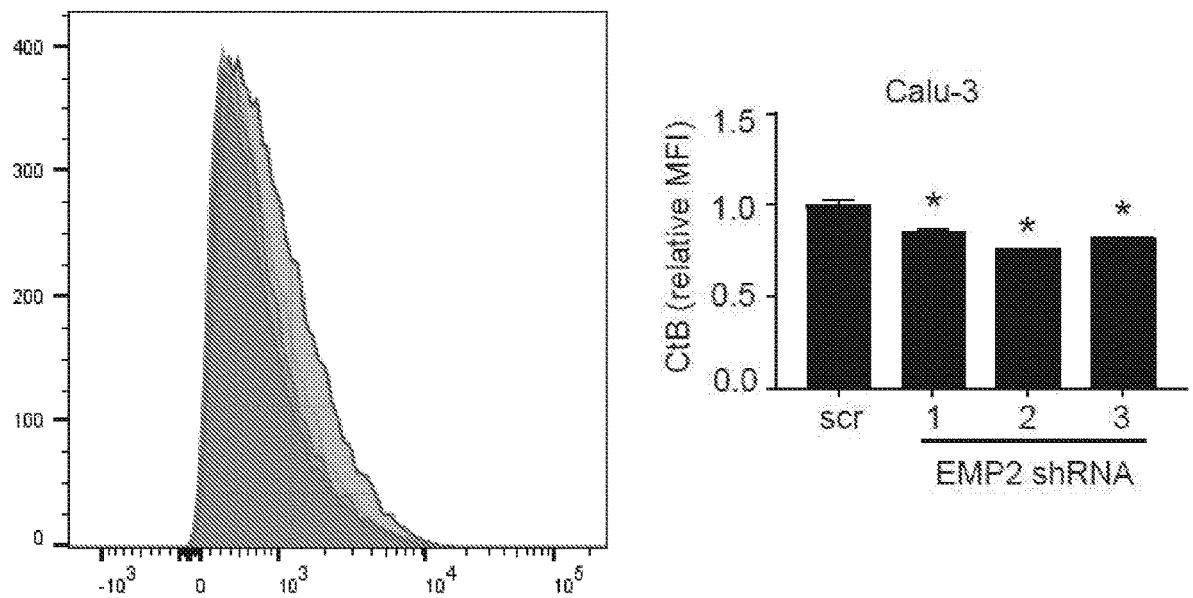
Figure 3C:
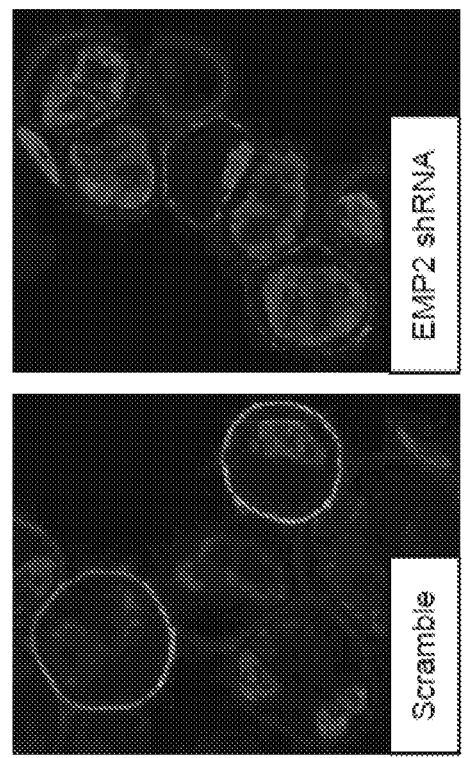
Figure 3D:
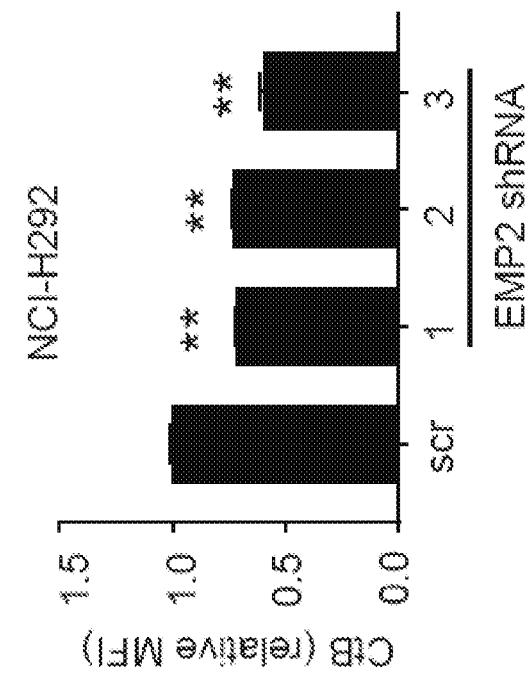
Figure 3F:
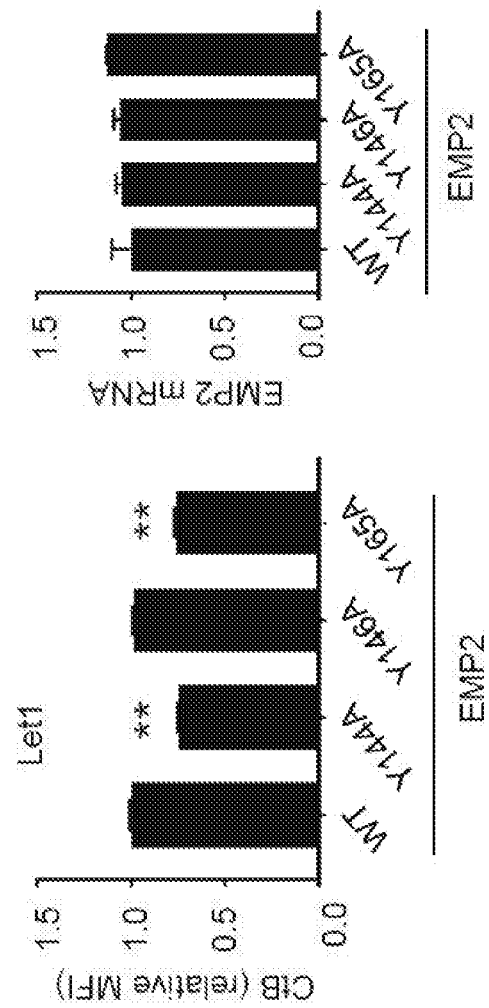
Figure 3E:
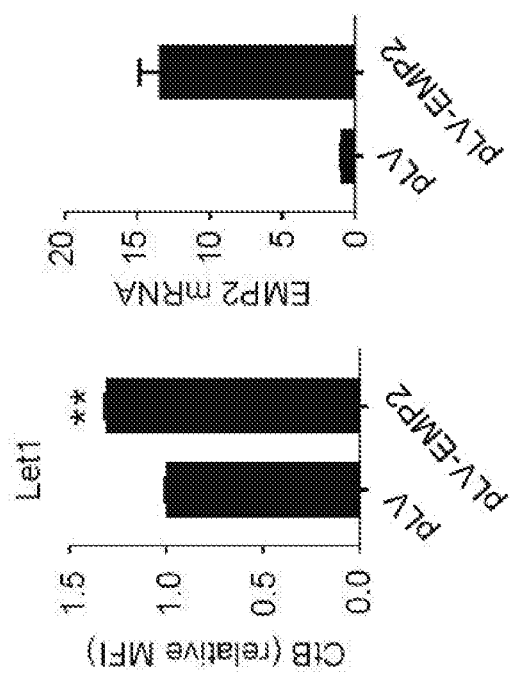

The multiple adhesion molecule changes in Emp2−/− AT1 cells suggested plasma membrane dysregulation as a potential unifying mechanism. Given that EMP2 supports lipid raft assembly in cell lines and some of the proteins implicated in TEM localize to rafts (4, 8), it was hypothesized that rafts might be abnormal in EMP2-deficient pulmonary epithelial cells. Consistent with this, it was found that primary murine AT1-like cells transdifferentiated in vitro from mouse lung digests displayed a significant reduction in surface binding of cholera toxin B (CtB) (FIG. 3A), a ligand for GM1 and other raft-localized gangliosides that has been used widely as a metric for raft mass (13). Raft mass was similarly reduced in EMP2-silenced Calu-3 cells (FIGS. 3B-3C) and H292 cells (FIG. 3D). Conversely, in Lett cells, an AT1-like cell line (20) in which we could not detect expression of native EMP2 protein by immunoblot, overexpression of EMP2 augmented CtB binding, indicating increased raft mass (FIG. 3E).

Cholesterol recognition/interaction amino-acid consensus (CRAC) motifs, with the sequence (L/V)-X1-5-(Y)-X1-5-(K/R) (where X1-5 is 1 to 5 of any amino acid and the central tyrosine is proposed to be critical) and inverted CRAC ('CARO') motifs are two amino acid sequences by which membrane proteins are proposed to bind to cholesterol (21). Both motifs are proposed to sequester and stabilize cholesterol in membranes and potentially to play an important role in assembly of cholesterol-rich rafts (22). The tetraspan family member PMP22 has a CRAC motif in its fourth transmembrane domain (23). Upon manual inspection, EMP2 was found to have only one potential CRAC sequence in, plus three potential CARC sequences near, its predicted fourth transmembrane domain (FIG. 11). the central tyrosine residue of the two CARCs nearest the transmembrane domain (Y144, Y146), as well as that of the CRAC motif (Y165), were mutated. Interestingly, Y144A and Y165A EMP2 mutants failed to support CtB binding in Lett cells to the degree of WT EMP2 protein (FIG. 3F). indicating that interactions of EMP2 with cholesterol in its fourth transmembrane domain are required for its raft-supporting function in AT1 cells.

These data show that EMP2 regulates AT1 cell raft integrity and that EMP2 interactions with cholesterol through its fourth transmembrane domain are required for its raft-supporting function.

Example 5

This example illustrates that EMP2-deficient mice have enhanced survival during bacterial pneumonia.

PMNs are critical for bacterial killing during pneumonia, but also cause bystander injury to the epithelium (4). To what degree PMNs eradicate bacteria in the alveolar lumen versus interstitium during pneumonia is unclear, but successful passage of bacteria through damaged pulmonary epithelium is associated with extrapulmonary dissemination and mortality (24).

A modest, statistically nonsignificant increase in bacterial burden was found in whole (non-lavaged) lung homogenates of Emp2−/− mice during infection with *K. pneumoniae* (FIG. 4A), and no consistent change in bacterial counts in BALF (not shown), collectively indicating grossly intact bacterial clearance in the infected Emp2−/− lung.

Figure 4B:
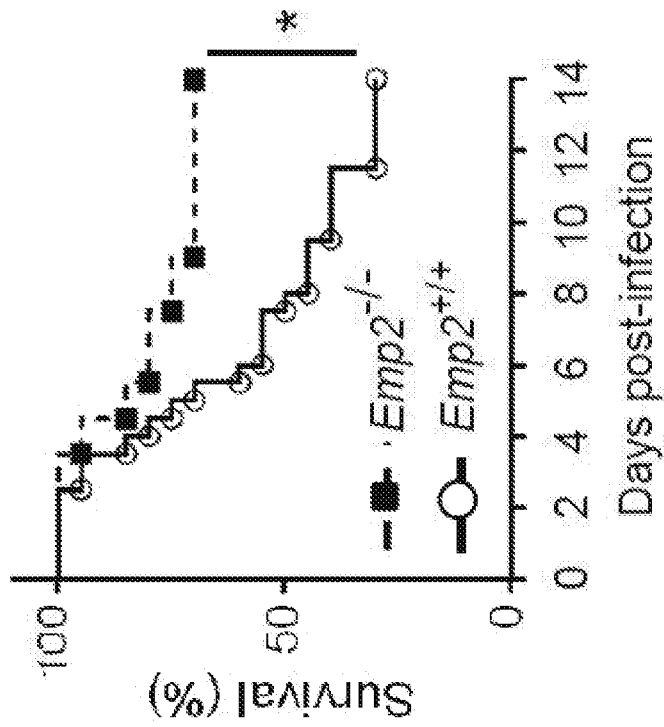
FIGS. 4A-4E illustrate that EMP2-null mice have reduced mortality and lung injury during bacterial pneumonia. (A) $Emp2^{+/+}$ and $Emp2^{-/-}$ mice were infected intratracheally (i.t.) with K. pneumoniae and then had bacterial colony forming units (CFUs) quantified in lung homogenates 24 h post-infection (N=6-7/genotype). (B) Survival was monitored in mice infected with i.t. K. pneumoniae (N=20/genotype). (C-D) BALF protein was measured in mice 24 h post-LPS (C) or K. pneumoniae (D) inhalation (N=5-6/genotype). (E) BALF cytokines and chemokines were quantified 24 h post-K. pneumoniae lung infection (N=6/genotype). Data are the mean±SEM and are representative of at least 3 independent experiments. *$P<0.05$, **$P<0.01$ by unpaired 2-tailed Student's test or log-rank test (survival).
Figure 4A:
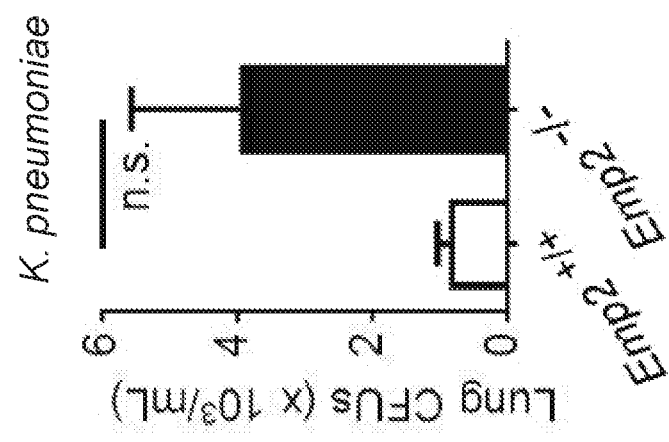
Figure 4E:
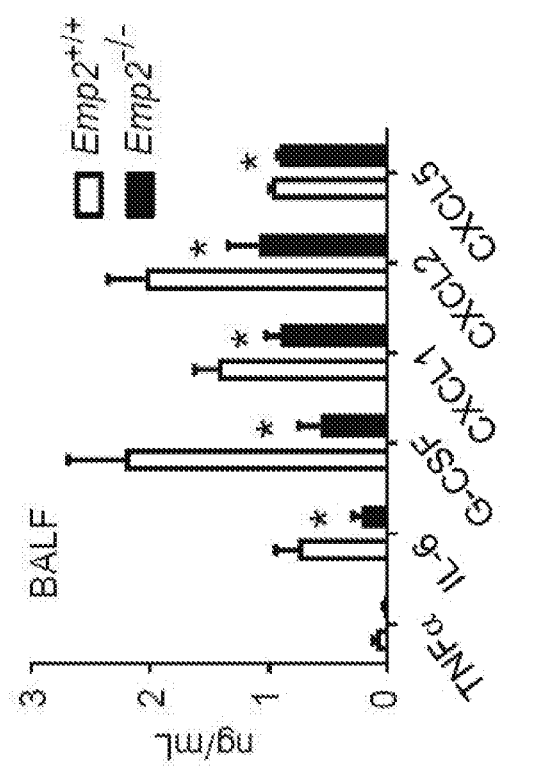
Figure 4D:
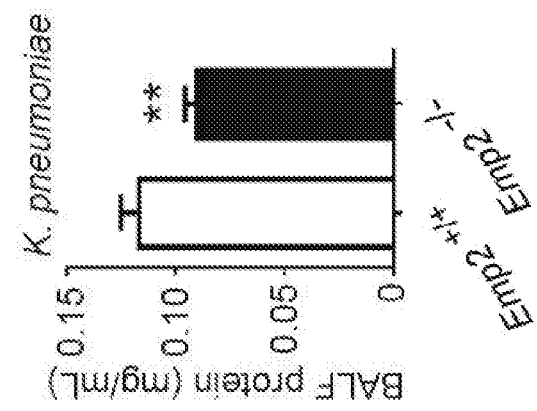
Figure 4C:
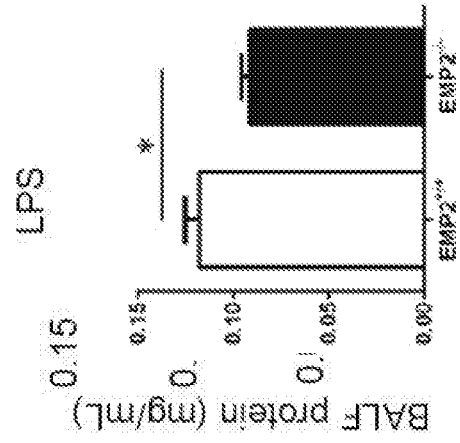
Figure 5A:
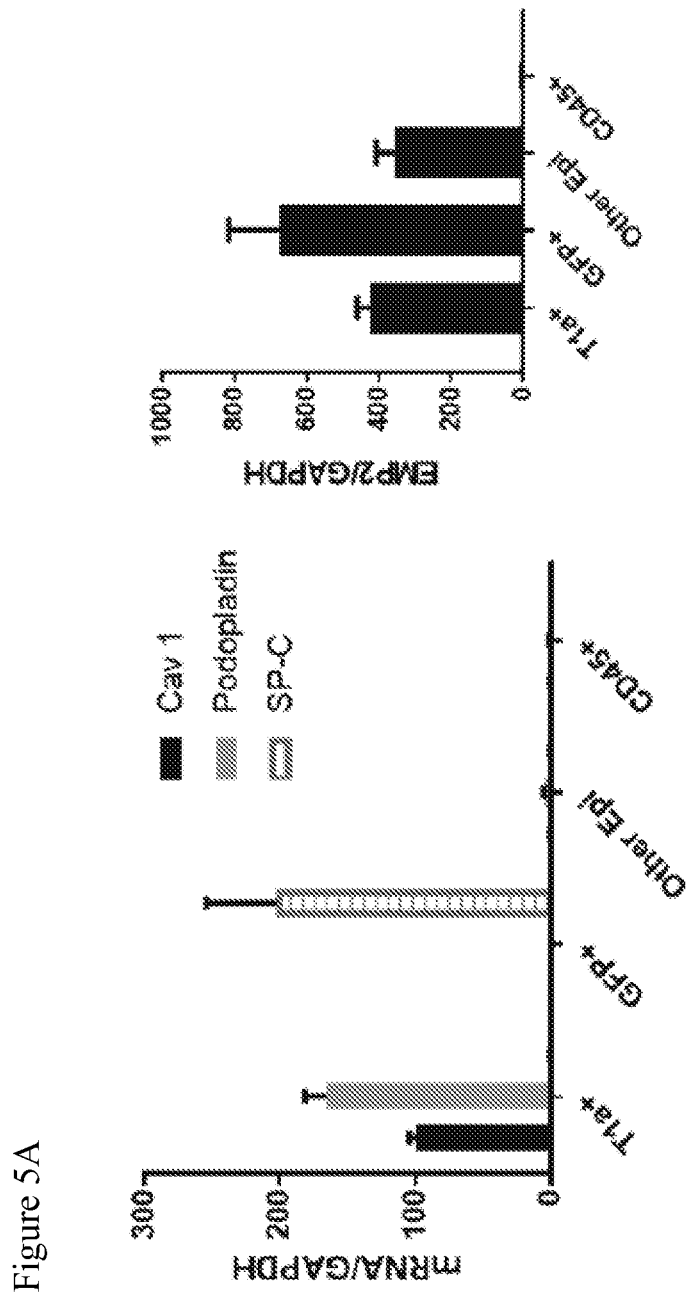
FIGS. 5A-5E illustrate EMP2 expression and alveolar epithelial cell gating by flow cytometry. (A) Lungs from SPC-GFP transgenic mice were digested for analysis. Lineage (Lin)-negative (CD31−CD34−), EpCAM+ cells that were T1α+ (AT1) cells, GFP+ (AT2) cells, T1α−GFP− (non-AT1/AT2 cells), or CD45+ (hematopoietic cells) were collected by fluorescence-activated cell sorting and then analyzed by RT-qPCR for caveolin-1 (AT1 marker), podoplanin (AT1 marker), surfactant protein C (SP-C, AT2 marker), and EMP2, as shown. (B) Representative flow cytometry gating corresponding to sort in panel A. (C) RT-qPCR for EMP2 mRNA was performed on alveolar macrophages collected by BAL and lung tissue from WT mice. (D) An alternative flow cytometry gating strategy for identification of lung epithelial cells is depicted. Lin-negative (CD31−CD34−CD45−), 7AAD− cells were gated for EpCAM positivity to identify epithelial cells, and then by Lysotracker (AT2) vs. T1α (AT1) to identify AT1, AT2, and non-AT1/AT2 lung epithelial cells. (E) Lung epithelial populations purified by the fluorescence-activated cell sorting gating strategy shown in panel D were analyzed by RT-qPCR for the targets shown. Data are the mean±SEM and are representative of at least 3 independent experiments.
Figure 5B:
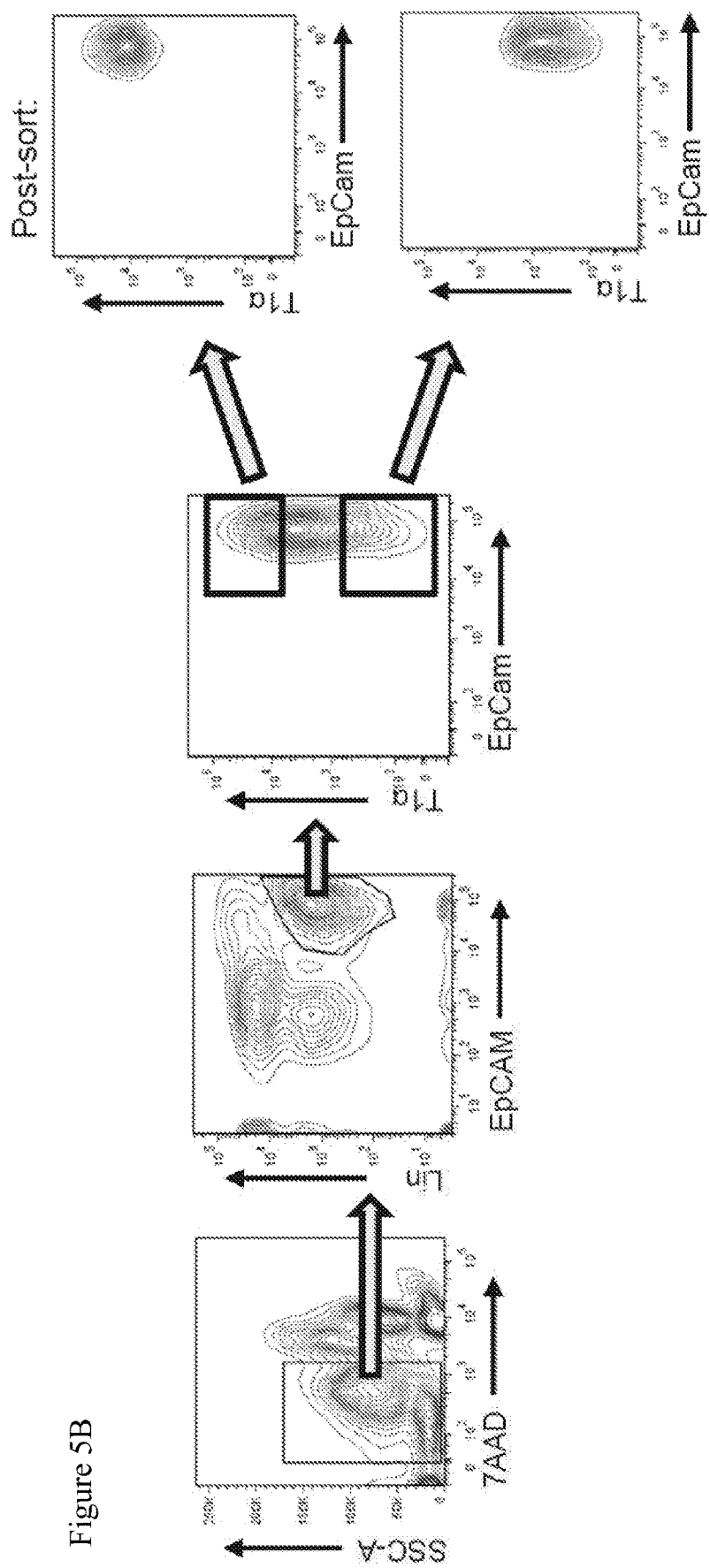
Figure 5C:
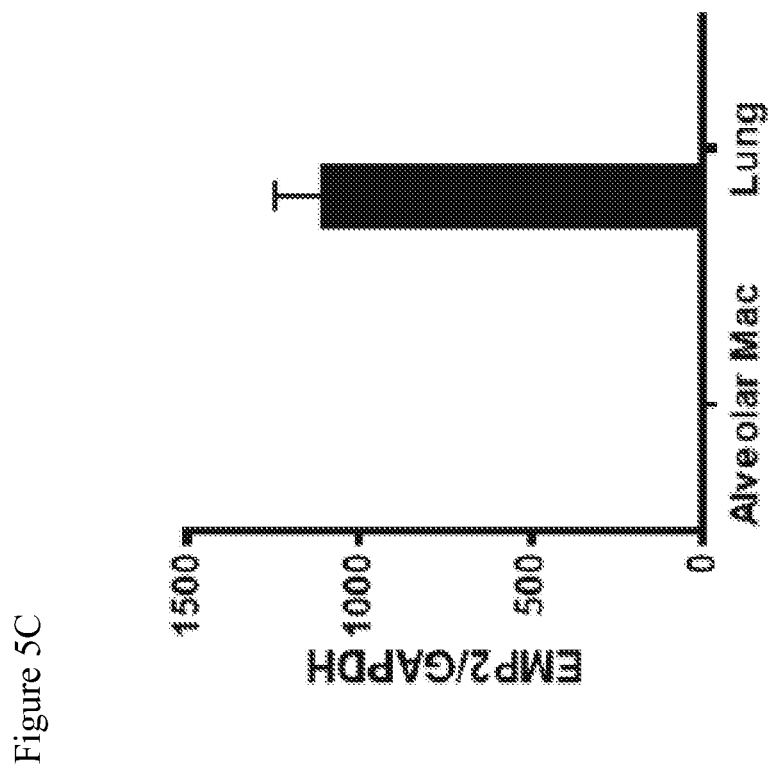
Figure 5D:
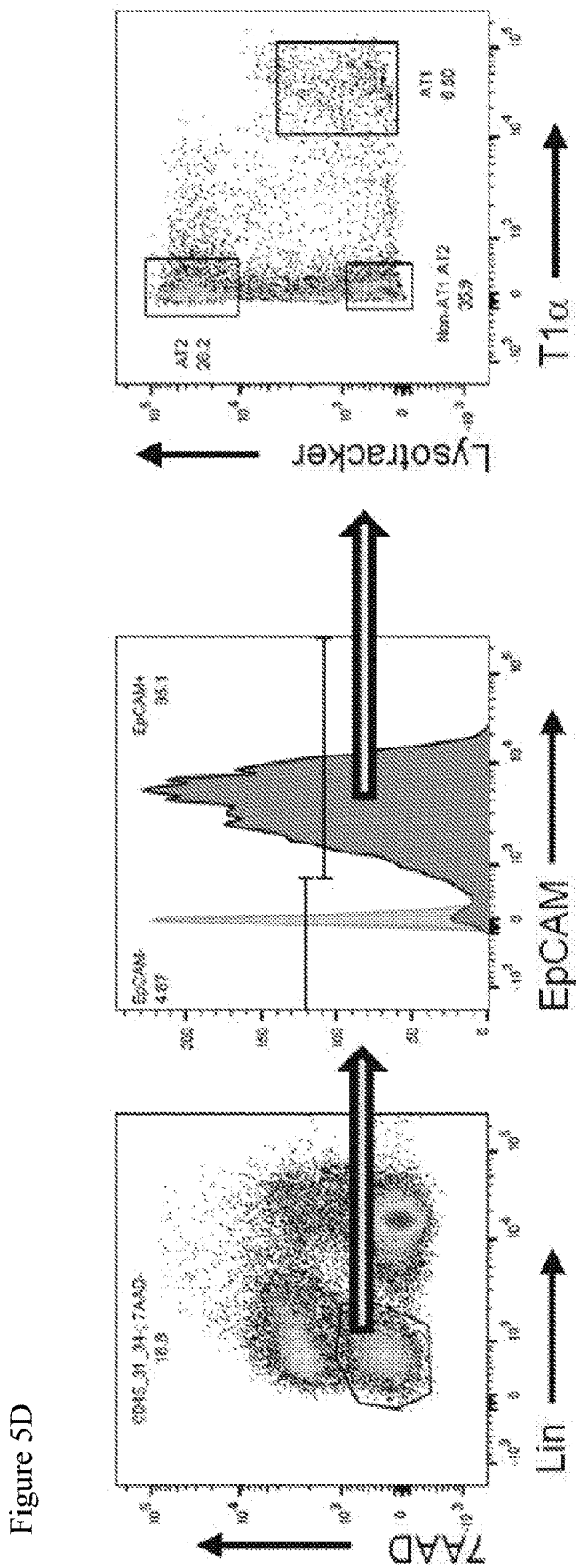
Figure 5E:
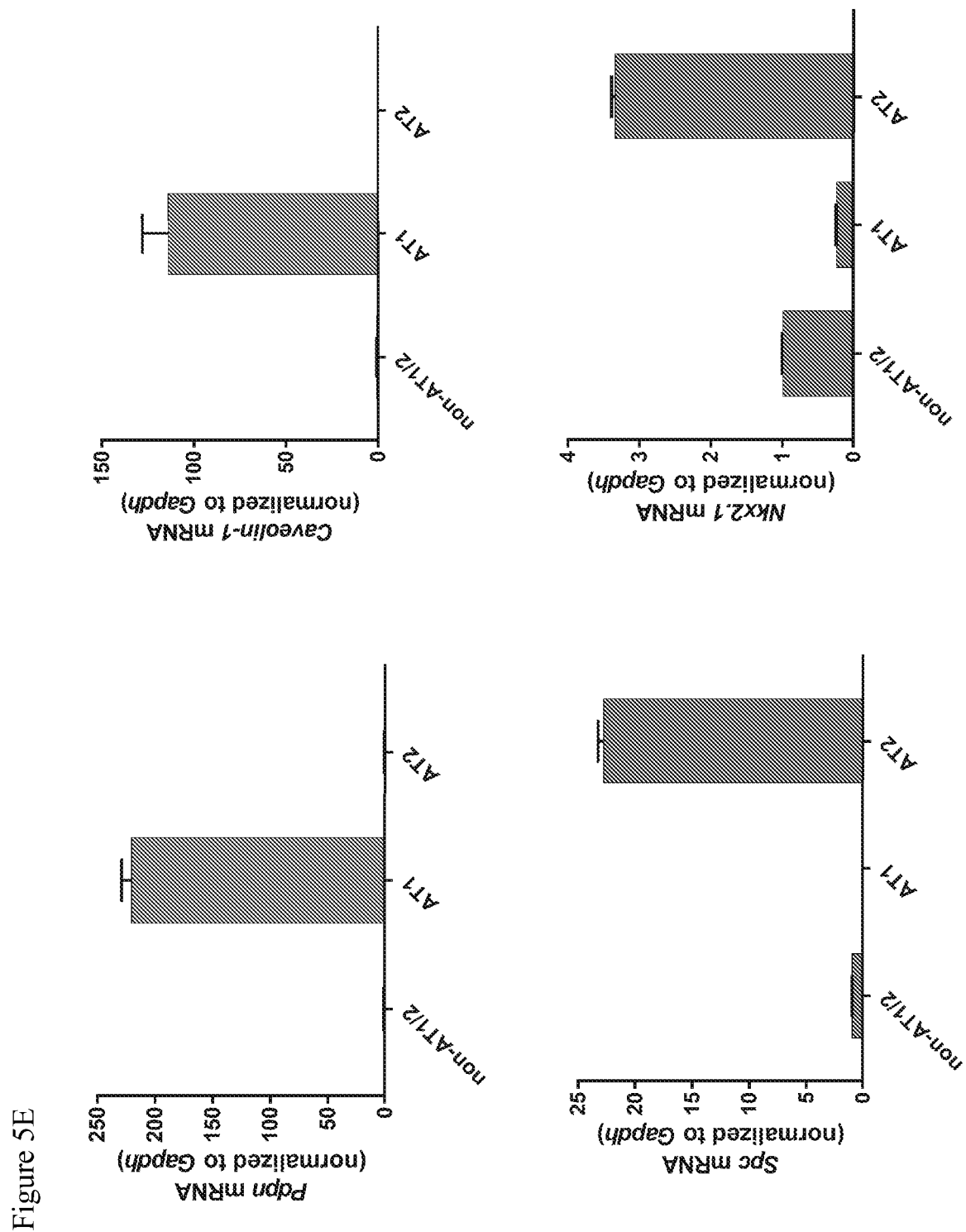

Surprisingly, Emp2−/− mice, however, exhibited increased survival during lung infection with *K. pneumoniae* compared to wild type counterparts (FIG. 4B). This was associated with attenuated injury to the alveolocapillary barrier, as indicated by reduced BALF protein (FIGS. 4C-4D). There was also a wide-ranging reduction in BALF pro-inflammatory cytokines at 24h post-infection (FIG. 4E), a time point at which Emp2−/− mice have significantly reduced alveolar PMNs but no change in bacterial burden in the lung (FIGS. 1B, 4A).

These data show that the increased cytokines in wild type mice derived either from PMNs or from other immune cells in the airway amplify the inflammatory signal, and that Emp2−/− mice show reduction in pro-inflammatory cytokines and are protected from inflammatory lung injury during pneumonia.

Example 6

This example illustrates that EMP2 deletion protects against bleomycin lung toxicity.

Bleomycin, a genotoxin, induces severe lung inflammation followed by lung fibrosis. Bleomycin inhalation in mice has thus been widely used as a temporal model of acute lung injury (days 1-5 post-exposure) and pulmonary fibrosis (day 21).

Figure 12:
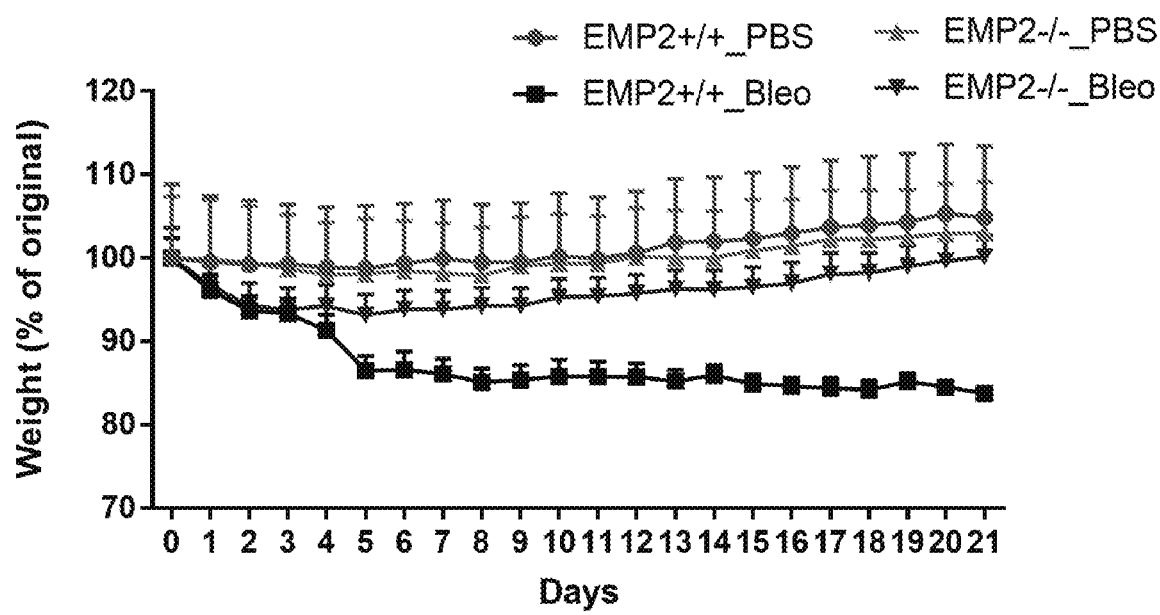
FIG. 12 shows that Emp2−/− mice are protected from weight loss after bleomycin inhalation. Emp2+/+ and Emp2−/− mice were intratracheally administered either 2 U/kg bleomycin ("bleo") or 1×PBS (control), and body weight was monitored for 21 days, as shown. Body weight was indexed to baseline weight, set at 100%. As shown, bleo-exposed Emp2−/− mice are dramatically protected from the weight loss seen in wt counterparts, with their body weight approximating that of mice exposed to PBS control. N=5 mice/genotype/treatment.

In order to determine whether EMP2 deletion protects against bleomycin lung toxicity, Emp2+/+ and Emp2−/− mice were exposed to either 2U/kg bleomycin or 1×PBS (control) via oropharyngeal aspiration into the lungs. Remarkably, whereas Emp2+/+mice suffered significant weight loss after inhaled bleomycin, likely due to severe lung inflammation, Emp2−/− mice displayed a weight profile similar to that of mice exposed to PBS control (FIG. 12).

Figure 13:
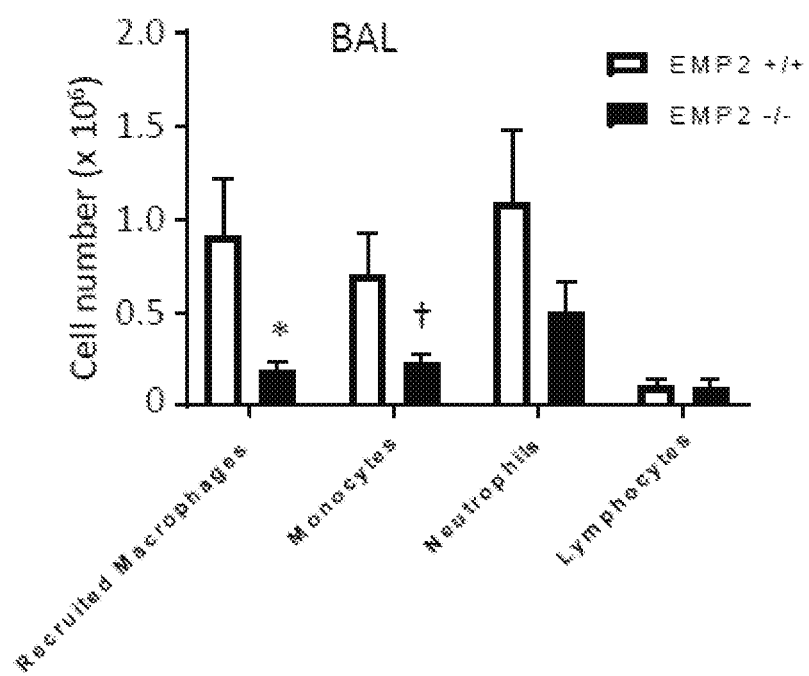
FIG. 13 shows that Emp2−/− mice have reduced influx of leukocytes to airspace after bleomycin inhalation. Emp2+/+ and Emp2−/− mice were given 2 U/kg bleomycin intratracheally. Five days later, the indicated cell types were quantified in bronchoalveolar lavage (BAL) fluid by flow cytometry. N=5 mice/genotype. Cell markers used to identify cells are shown in table. *, P<0.05; †, P=0.06.
Figure 14A:
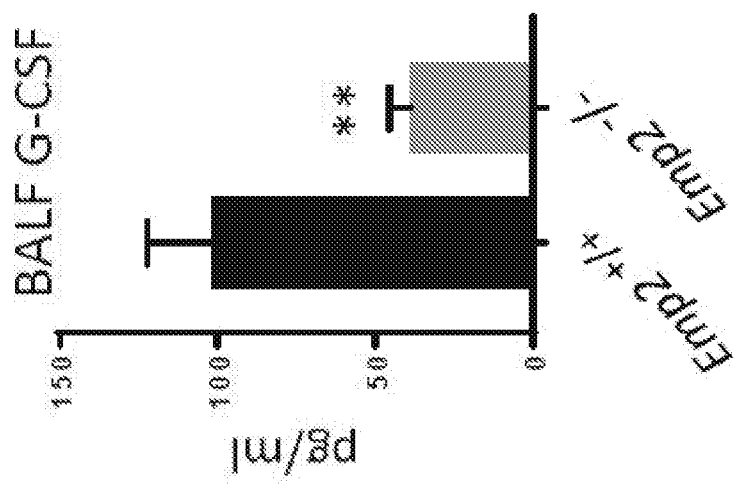
FIGS. 14A-14E show that Emp2−/− mice have reduced pro-inflammatory cytokines and markers of microvascular injury in the airspace after inhaled bleomycin. Emp2+/+ and Emp2−/− mice were given 2 U/kg bleomycin intratracheally. Five days later, the indicated cytokines (IL-6, IL-12, G-CSF or MCP-1) were measured in bronchoalveolar lavage fluid (BALF) by Bioplex assay (A-D). Albumin, a marker of microvascular lung injury, was measured by ELISA (E). N=10-12/genotype. *, P<0.05; **, P<0.01.
Figure 14B:
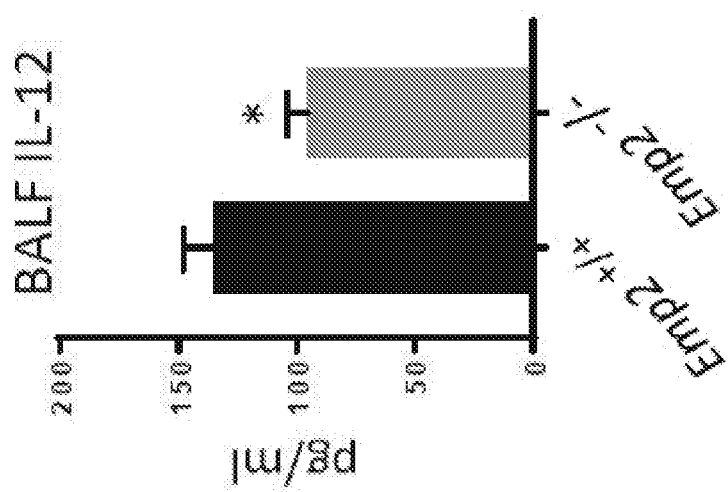
Figure 14C:
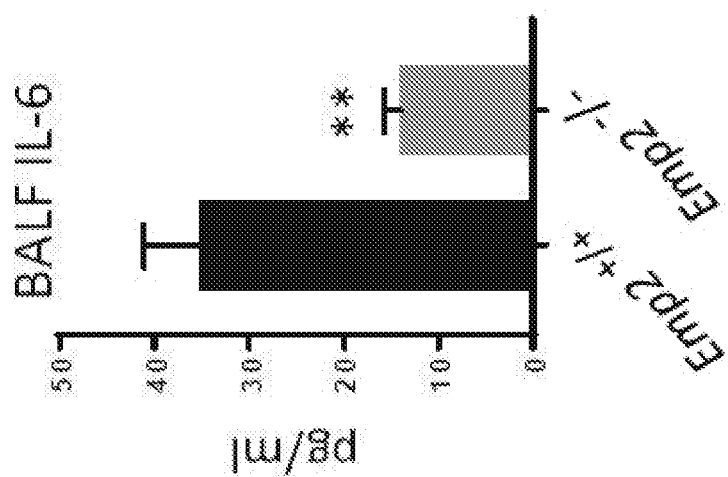
Figure 14E:
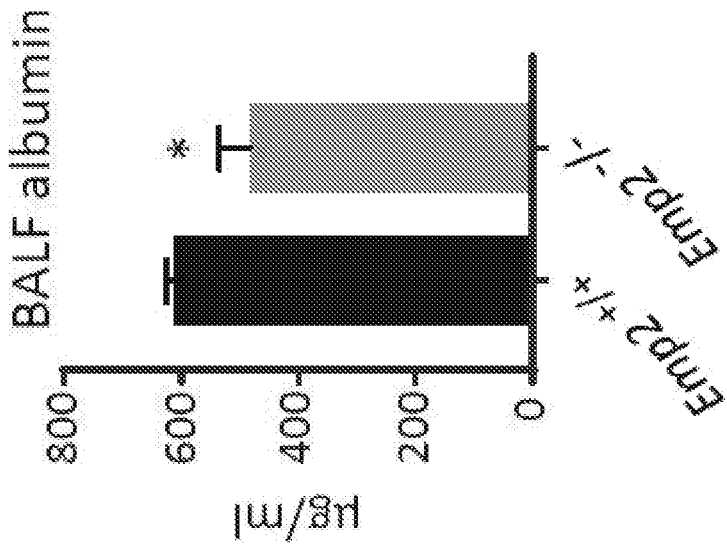
Figure 14D:
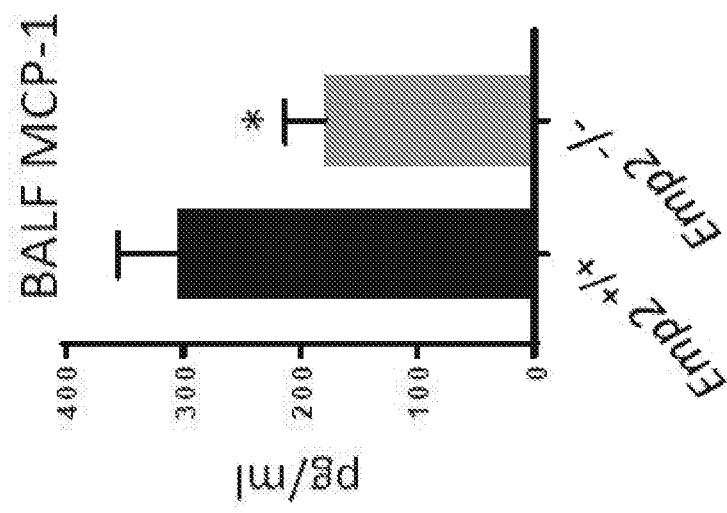

In order to profile lung inflammatory responses to bleomycin, the lungs of mice 5d post-exposure were evaluated. Emp2−/− mice exhibited a reduction in the airspace of monocytes and monocyte-derived ('recruited') alveolar macrophages compared to controls (FIG. 13). Emp2−/− mice also showed a reduction in neutrophils recruited to the airspace. Multiple pro-inflammatory cytokines were also lower in the Emp2–/– airway post-bleomycin, indicating reduced lung inflammation (FIGS. 14A-14E). In addition, airspace fluid albumin, a marker of microvascular leak, was lower in Emp2–/– mice than in controls, indicating attenuated lung injury (FIGS. 14A-14E).

In order to determine whether EMP2 deletion is protective against bleomycin-induced lung fibrosis, lungs from mice on day 21 post-exposure were harvested. Emp2–/– lungs had a significant reduction in lung hydroxyproline, a surrogate measure of collagen, indicating reduced fibrosis (FIG. 15A). Consistent with this, the increase in gene expression of collagen and fibronectin induced by bleomycin in wt lungs was nearly abolished in Emp2–/– lungs (FIG. 15B). Expression of (myo)fibroblast-associated genes was similarly attenuated in Emp2–/– lungs (FIG. 15C), as was expression of the cytokine IL-6 (FIG. 15D).

Taken together, these findings indicate that EMP2 deletion in mice protects against multiple outcomes of bleomycin inhalation, including constitutional signs (weight loss), lung inflammation, lung injury, and lung fibrosis.

Example 7

This example illustrates that targeting EMP2 by administration of an anti-EMP2 agent reduces airspace neutrophilia induced by LPS in wild type mice.

In order to evaluate the potential for targeting EMP2 in vivo as a strategy for reducing lung inflammation, a neutralizing anti-EMP2 scFv, KS83, was synthesized and purified. KS83, which targets the second extracellular loop of mouse EMP2, has been shown to bind native EMP2 by flow cytometry (Shimazaki K. et al., Clin Cancer Res 2008; 14:7367-7377) and to reduce EMP2 expression in the mouse genital tract in vivo (Shimazaki K et al., FEMS Immunol Med Microbiol 2009; 55(2):240-9). Mouse IgG, Fab fragment (#015-000-007, Jackson ImmunoResearch, West Grove, Pa.) was used as a structurally similar control treatment.

Figure 16:
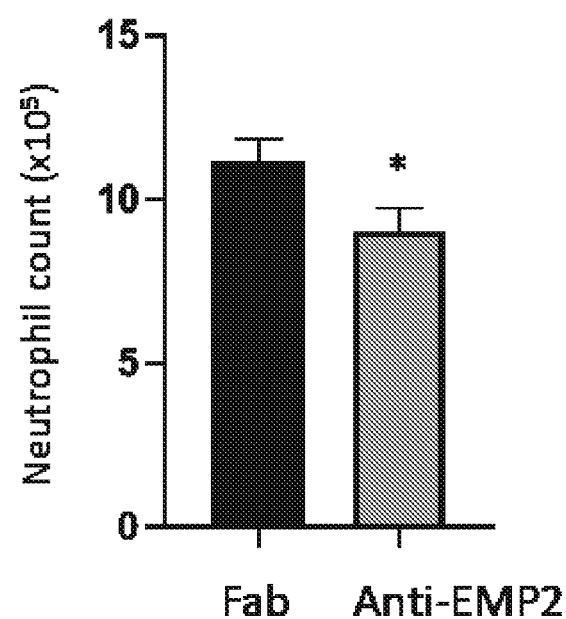
FIG. 16 shows that EMP2 blockade by administration of an anti-EMP2 antibody reduces LPS-induced airway neutrophilia in wild type mice. Neutrophil counts in the bronchoalveolar lavage fluid of wild type mice pretreated either with an anti-EMP2 antibody or with a control Fab fragment of IgG, at 24 h post-LPS aerosol inhalation are shown. N=15/treatment. *, P<0.05.

C57BL/6 (Wild Type) mice were pre-treated by oropharyngeal aspiration into the lungs with 250 μg of Fab (control) or anti-EMP2 scFv at –24 h and –2 h prior to exposure to *E. coli* LPS aerosol (300 μg/ml, 30 minutes). At 24h post-LPS inhalation, neutrophils were quantified in the bronchoalveolar lavage fluid. As shown in the FIG. 16, anti-EMP2-treated mice were found to have a statistically significant reduction in airspace neutrophils compared to the controls.

REFERENCES

1. Rossaint, J., and Zarbock, A. 2013. Tissue-specific neutrophil recruitment into the lung, liver, and kidney. *J Innate Immun* 5:348-357.
2. Burns, A. R., Smith, C. W., and Walker, D. C. 2003. Unique structural features that influence neutrophil emigration into the lung. *Physiol Rev* 83:309-336.
3. Mizgerd, J. P. 2002. Molecular mechanisms of neutrophil recruitment elicited by bacteria in the lungs. *Semin Immunol* 14:123-132.
4. Zemans, R. L., Colgan, S. P., and Downey, G. P. 2009. Transepithelial migration of neutrophils: mechanisms and implications for acute lung injury. *Am J Respir Cell Mol Biol* 40:519-535.
5. Li, Q., Park, P. W., Wilson, C. L., and Parks, W. C. 2002. Matrilysin shedding of syndecan-1 regulates chemokine mobilization and transepithelial efflux of neutrophils in acute lung injury. *Cell* 111:635-646.
6. Brazil, J. C., and Parkos, C. A. 2016. Pathobiology of neutrophil-epithelial interactions. *Immunol Rev* 273:94-111.
7. Wadehra, M., Iyer, R., Goodglick, L., and Braun, J. 2002. The tetraspan protein epithelial membrane protein-2 interacts with beta1 integrins and regulates adhesion. *J Biol Chem* 277:41094-41100.
8. Wadehra, M., Su, H., Gordon, L. K., Goodglick, L., and Braun, J. 2003. The tetraspan protein EMP2 increases surface expression of class I major histocompatibility complex proteins and susceptibility to CTL-mediated cell death. *Clin Immunol* 107:129-136.
9. Wadehra, M., Goodglick, L., and Braun, J. 2004. The tetraspan protein EMP2 modulates the surface expression of caveolins and glycosylphosphatidyl inositol-linked proteins. *Mol Biol Cell* 15:2073-2083.
10. Wadehra, M., Forbes, A., Pushkarna, N., Goodglick, L., Gordon, L. K., Williams, C. J., and Braun, J. 2005. Epithelial membrane protein-2 regulates surface expression of alphavbeta3 integrin in the endometrium. *Dev Biol* 287:336-345.
11. Fu, M., Rao, R., Sudhakar, D., Hogue, C. P., Rutta, Z., Morales, S., Gordon, L. K., Braun, J., Goodglick, L., and Wadehra, M. 2011. Epithelial membrane protein-2 promotes endometrial tumor formation through activation of FAK and Src. *PLoS One* 6:e19945.
12. Dahlin, K., Mager, E. M., Allen, L., Tigue, Z., Goodglick, L., Wadehra, M., and Dobbs, L. 2004. Identification of genes differentially expressed in rat alveolar type I cells. *Am J Respir Cell Mol Biol* 31:309-316.
13. Fessler, M. B., and Parks, J. S. 2011. Intracellular lipid flux and membrane microdomains as organizing principles in inflammatory cell signaling. *J Immunol* 187:1529-1535.
14. Yamamoto, K., Ferrari, J. D., Cao, Y., Ramirez, M. I., Jones, M. R., Quinton, L. J., and Mizgerd, J. P. 2012. Type I alveolar epithelial cells mount innate immune responses during pneumococcal pneumonia. *J Immunol* 189:2450-2459.
15. Humlicek, A. L., Pang, L., and Look, D. C. 2004. Modulation of airway inflammation and bacterial clearance by epithelial cell ICAM-1. *Am J Physiol Lung Cell Mol Physiol* 287:L598-607.
16. Sumagin, R., Robin, A. Z., Nusrat, A., and Parkos, C. A. 2014. Transmigrated neutrophils in the intestinal lumen engage ICAM-1 to regulate the epithelial barrier and neutrophil recruitment. *Mucosal Immunol* 7:905-915.
17. Moon, C., Han, J. R., Park, H. J., Hah, J. S., and Kang, J. L. 2009. Synthetic RGDS peptide attenuates lipopolysaccharide-induced pulmonary inflammation by inhibiting integrin signaled MAP kinase pathways. *Respir Res* 10:18.
18. Ridger, V. C., Wagner, B. E., Wallace, W. A., and Hellewell, P. G. 2001. Differential effects of CD18, CD29, and CD49 integrin subunit inhibition on neutrophil migration in pulmonary inflammation. *J Immunol* 166:3484-3490.
19. Forbes, A., Wadehra, M., Mareninov, S., Morales, S., Shimazaki, K., Gordon, L. K., and Braun, J. 2007. The tetraspan protein EMP2 regulates expression of caveolin-1. *J Biol Chem* 282:26542-26551.
20. Rosenberger, C. M., Podyminogin, R. L., Askovich, P. S., Navarro, G., Kaiser, S. M., Sanders, C. J., McClaren, J. L., Tam, V. C., Dash, P., Noonan, J. G., 2014. Characterization of innate responses to influenza virus infection in a novel lung type I epithelial cell model. *J Gen Virol* 95:350-362.

21. Fantini, J., and Barrantes, F. J. 2013. How cholesterol interacts with membrane proteins: an exploration of cholesterol-binding sites including CRAC, CARC, and tilted domains. *Front Physiol* 4:31.
22. Epand, R. M. 2006. Cholesterol and the interaction of proteins with membrane domains. *Prog Lipid Res* 45:279-294.
23. Sedzik, J., Jastrzebski, J. P., and Ikenaka, K. 2013. Sequence motifs of myelin membrane proteins: towards the molecular basis of diseases. *J Neurosci Res* 91:479-493.
24. Rai, P., Parrish, M., Tay, I. J., Li, N., Ackerman, S., He, F., Kwang, J., Chow, V. T., and Engelward, B. P. 2015. Streptococcus pneumoniae secretes hydrogen peroxide leading to DNA damage and apoptosis in lung cells. *Proc Natl Acad Sci USA* 112:E3421-3430.
25. Kim, H. J., Henke, C. A., Savik, S. K., and Ingbar, D. H. 1997. Integrin mediation of alveolar epithelial cell migration on fibronectin and type I collagen. *Am J Physiol* 273:L134-141.
26. Wilson, H. L., Wilson, S. A., Surprenant, A., and North, R. A. 2002. Epithelial membrane proteins induce membrane blebbing and interact with the P2X7 receptor C terminus. *J Biol Chem* 277:34017-34023.
27. Barth, K., Blasche, R., Neisser, A., Bramke, S., Frank, J. A., and Kasper, M. 2016. P2X7R-dependent regulation of glycogen synthase kinase 3beta and claudin-18 in alveolar epithelial type I cells of mice lung. *Histochem Cell Biol* 146:757-768.
28. Chung, L. K., Bhatt, N. S., Lagman, C., Pelargos, P. E., Qin, Y., Gordon, L. K., Wadehra, M., and Yang, I. 2017. Epithelial membrane protein 2: Molecular interactions and clinical implications. *J Clin Neurosci* 44:84-88.
29. Williams, C. J., Chu, A., Jefferson, W. N., Casero, D., Sudhakar, D., Khurana, N., Hogue, C. P., Aryasomayajula, C., Patel, P., Sullivan, P., 2017. Epithelial membrane protein 2 (EMP2) deficiency alters placental angiogenesis, mimicking features of human placental insufficiency. *J Pathol* 242:246-259.
30. Chapman, H. A., Li, X., Alexander, J. P., Brumwell, A., Lorizio, W., Tan, K., Sonnenberg, A., Wei, Y., and Vu, T. H. 2011. Integrin alpha6beta4 identifies an adult distal lung epithelial population with regenerative potential in mice. *J Clin Invest* 121:2855-2862.
31. Jansing, N. L., McClendon, J., Henson, P. M., Tuder, R. M., Hyde, D. M., and Zemans, R. L. 2017. Unbiased Quantitation of ATII to ATI Cell Transdifferentiation During Repair After Lung Injury in Mice. *Am J Respir Cell Mol Biol.*
32. Draper, D. W., Madenspacher, J. H., Dixon, D., King, D. H., Remaley, A. T., and Fessler, M. B. 2010. ATP-binding cassette transporter G1 deficiency dysregulates host defense in the lung. *Am J Respir Crit Care Med* 182:404-412.
33. Draper, D. W., Gowdy, K. M., Madenspacher, J. H., Wilson, R. H., Whitehead, G. S., Nakano, H., Pandiri, A. R., Foley, J. F., Remaley, A. T., Cook, D. N., 2012. ATP binding cassette transporter G1 deletion induces IL-17-dependent dysregulation of pulmonary adaptive immunity. *J Immunol* 188:5327-5336.
34. Lai, L., Azzam, K. M., Lin, W. C., Rai, P., Lowe, J. M., Gabor, K. A., Madenspacher, J. H., Aloor, J. J., Parks, J. S., Naar, A. M., 2016. MicroRNA-33 Regulates the Innate Immune Response via ATP Binding Cassette Transporter-mediated Remodeling of Membrane Microdomains. *J Biol Chem* 291:19651-19660.
35. Demaio, L., Tseng, W., Balverde, Z., Alvarez, J. R., Kim, K. J., Kelley, D. G., Senior, R. M., Crandall, E. D., and Borok, Z. 2009. Characterization of mouse alveolar epithelial cell monolayers. *Am J Physiol Lung Cell Mol Physiol* 296:L1051-1058.
36. Dobbs, L. G., and Mason, R. J. 1979. Pulmonary alveolar type II cells isolated from rats. Release of phosphatidylcholine in response to beta-adrenergic stimulation. *J Clin Invest* 63:378-387.
37. Barletta, K. E., Cagnina, R. E., Wallace, K. L., Ramos, S. I., Mehrad, B., and Linden, J. 2012. Leukocyte compartments in the mouse lung: distinguishing between marginated, interstitial, and alveolar cells in response to injury. *J Immunol Methods* 375:100-110.
38. Lyons-Cohen, M. R., Thomas, S. Y., Cook, D. N., and Nakano, H. 2017. Precision-cut Mouse Lung Slices to Visualize Live Pulmonary Dendritic Cells. *J Vis Exp.*
39. Stripp, B. R., Reynolds, S. D., Boe, I. M., Lund, J., Power, J. H., Coppens, J. T., Wong, V., Reynolds, P. R., and Plopper, C. G. 2002. Clara cell secretory protein deficiency alters clara cell secretory apparatus and the protein composition of airway lining fluid. *Am J Respir Cell Mol Biol* 27:170-178.
40. Rosenberger, C. M., Podyminogin, R. L., Askovich, P. S., Navarro, G., Kaiser, S. M., Sanders, C. J., McClaren, J. L., Tam, V. C., Dash, P., Noonan, J. G., 2014. Characterization of innate responses to influenza virus infection in a novel lung type I epithelial cell model. *J Gen Virol* 95:350-362.
41. Frank, S. B., Schulz, V. V., and Miranti, C. K. 2017. A streamlined method for the design and cloning of shRNAs into an optimized Dox-inducible lentiviral vector. *BMC Biotechnol* 17:24.
42. Zemans, R. L., Briones, N., Campbell, M., McClendon, J., Young, S. K., Suzuki, T., Yang, I. V., De Langhe, S., Reynolds, S. D., Mason, R. J., 2011. Neutrophil transmigration triggers repair of the lung epithelium via beta-catenin signaling. *Proc Natl Acad Sci USA* 108:15990-15995.
43. Fessler, M. B., Arndt, P. G., Frasch, S. C., Lieber, J. G., Johnson, C. A., Murphy, R. C., Nick, J. A., Bratton, D. L., Malcolm, K. C., and Worthen, G. S. 2004. Lipid rafts regulate lipopolysaccharide induced activation of Cdc42 and inflammatory functions of the human neutrophil. *J Biol Chem* 279:39989-39998.
44. Parkos, C. A., Delp, C., Arnaout, M. A., and Madara, J. L. 1991. Neutrophil migration across a cultured intestinal epithelium. Dependence on a CD11b/CD18-mediated event and enhanced efficiency in physiological direction. *J Clin Invest* 88:1605-1612.
45. Chowdhury, S. M., Zhu, X., Aloor, J. J., Azzam, K. M., Gabor, K. A., Ge, W., Addo, K. A., Tomer, K. B., Parks, J. S., and Fessler, M. B. 2015. Proteomic Analysis of ABCA1-Null Macrophages Reveals a Role for Stomatin-Like Protein-2 in Raft Composition and Toll-Like Receptor Signaling. *Mol Cell Proteomics* 14:1859-1870.
46. Baier, C. J., Fantini, J., and Barrantes, F. J. 2011. Disclosure of cholesterol recognition motifs in transmembrane domains of the human nicotinic acetylcholine receptor. *Sci Rep* 1:69.
47. Fantini, J., and Barrantes, F. J. 2013. How cholesterol interacts with membrane proteins: an exploration of cholesterol-binding sites including CRAC, CARC, and tilted domains. *Front Physiol* 4:31.
48. Shimazaki K., Lepin E. J., Wei B., Nagy A. K., Coulam C. P., Mareninov S., Fu M., Wu A. M., Marks J. D., Braun J., Gordon L. K. and Wadehra M. Diabodies Targeting Epithelial Membrane Protein 2 Reduce Tumorigenicity of Human Endometrial Cancer Cell Lines. *Clin. Cancer Res.* 14:7367-7377

49. Shimazaki K., Chan A. M., Moniz R. J., Wadehra M., Nagy A., Coulam C. P., Mareninov S., Lepin E. J., Wu A. M., Kelly K. A., Braun J. and Gordon L. K. Blockade of epithelial membrane protein 2 (EMP2) abrogates infection of *Chlamydia muridarum* murine genital infection model. *FEMS Immunol. Med. Microbial.* 55(2):240-49.

The invention claimed is:

1. A method of treating or preventing a lung disorder in a subject in need thereof, comprising administering to the subject a composition comprising an agent that modulates the activity and/or expression of Epithelial Membrane Protein 2 (EMP2),
   wherein the agent is
   (a) an anti-EMP2 antibody selected from the group consisting of PG101, KS83, KS49, KS41, KS89, and a combination thereof, or an antigen-binding fragment thereof; or
   (b) a small interfering RNA (siRNA) capable of binding to an EMP2-encoding nucleotide sequence; or
   (c) an antisense oligonucleotide capable of binding to the EMP2-encoding nucleotide sequence, and
   wherein the lung disorder is
   (i) an acute disease selected from the group consisting of acute lung injury, acute respiratory distress syndrome, pneumonia, viral infection, and airway hyperresponsiveness;
   (ii) a neutrophil-dependent lung disorder;
   (iii) an epithelial lipid raft-dependent and/or caveolae-dependent lung disease;
   (iv) a TGF-β (Transforming growth factor beta)-mediated lung disorder selected from the group consisting of pulmonary fibrosis and acute lung injury;
   (v) an eosinophil-dependent lung disorder selected from the group consisting of asthma, acute eosinophilic pneumonia, and chronic eosinophilic pneumonia; or a monocyte-dependent lung disorder selected from the group consisting of lung fibrosis and acute lung injury; or a lymphocyte-dependent lung disorder selected from the group consisting of lymphocytic interstitial pneumonia and lymphocytic bronchiolitis;
   (vi) idiopathic pulmonary fibrosis comprising epithelium-matrix interaction;
   (vii) a chronic disease selected from the group consisting of chronic obstructive pulmonary disease (COPD), bronchiectasis, radiation- or chemotherapeutic-induced pneumonitis, idiopathic or induced interstitial lung disease, bronchopulmonary dysplasia, and lung fibrosis;
   (viii) a lung disorder due to exposure to a toxic agent selected from the group consisting of a bioterroristic agent, an occupational hazardous agent and an environmental pollutant or
   (ix) chemical pneumonitis due to chemical or acid or hydrocarbon aspiration; or chemical pneumonitis due to smoke inhalation.

2. The method of claim 1, wherein the anti-EMP2 antibody is KS83.

3. The method of claim 1, wherein the composition is administered to the subject systemically.

4. The method of claim 1, wherein the composition is administered to the subject parenterally.

5. The method claim 1, wherein the composition is administered to the subject topically, intranasally, intravenously, subcutaneously, intramuscularly, intradermally, or intraperitoneally.

6. The method of claim 1, wherein the composition is administered to the subject by inhalation.

7. The method of claim 6, wherein the composition is administered by a nebulizer or an inhaler.

8. The method of claim 1, wherein the composition is formulated as a nasal spray, gel, ointment, liquid, suspension, aerosol, tablet, pill or powder.

9. The method of claim 1, wherein the agent is in an amount sufficient to reduce intra-airway leukocyte accumulation in the subject.

10. The method of claim 1, wherein the subject is an infant at risk for acute lung injury due to meconium aspiration or prematurity.

11. A method to target a molecule to alveolar epithelial type 1 cells in a subject with a lung disorder comprising co-administering the molecule with an agent that binds EMP2, wherein the agent is an anti-EMP2 antibody selected from the group consisting of PG101, KS83, KS49, KS41, KS89, and a combination thereof, or an antigen-binding fragment thereof, wherein the lung disorder is
  (i) an acute disease selected from the group consisting of acute lung injury, acute respiratory distress syndrome, pneumonia, viral infection, and airway hyperresponsiveness;
  (ii) a neutrophil-dependent lung disorder;
  (iii) an epithelial lipid raft-dependent and/or caveolae-dependent lung disease;
  (iv) a TGF-β (Transforming growth factor beta)-mediated lung disorder selected from the group consisting of pulmonary fibrosis and acute lung injury;
  (v) an eosinophil-dependent lung disorder selected from the group consisting of asthma, acute eosinophilic pneumonia, and chronic eosinophilic pneumonia; or a monocyte-dependent lung disorder selected from the group consisting of lung fibrosis and acute lung injury; or a lymphocyte-dependent lung disorder selected from the group consisting of lymphocytic interstitial pneumonia and lymphocytic bronchiolitis;
  (vi) idiopathic pulmonary fibrosis comprising epithelium-matrix interaction;
  (vii) a chronic disease selected from the group consisting of chronic obstructive pulmonary disease (COPD), bronchiectasis, radiation- or chemotherapeutic-induced pneumonitis, idiopathic or induced interstitial lung disease, bronchopulmonary dysplasia, and lung fibrosis;
  (viii) a lung disorder due to exposure to a toxic agent selected from the group consisting of a bioterroristic agent, an occupational hazardous agent and an environmental pollutant or
  (ix) chemical pneumonitis due to chemical or acid or hydrocarbon aspiration; or chemical pneumonitis due to smoke inhalation.

* * * * *

```
                        SEQUENCE LISTING

<160> NUMBER OF SEQ ID NOS: 3

<210> SEQ ID NO 1
<211> LENGTH: 172
<212> TYPE: PRT
<213> ORGANISM: Mus musculus

<400> SEQUENCE: 1

Met Leu Val Ile Leu Ala Phe Ile Ile Val Phe His Ile Val Ser Thr
1               5                   10                  15

Ala Leu Leu Phe Ile Ser Thr Ile Asp Asn Ala Trp Trp Val Gly Asp
            20                  25                  30

Ser Phe Ser Ala Asp Leu Trp Arg Val Cys Thr Asn Ser Thr Asn Cys
        35                  40                  45

Thr Glu Ile Asn Glu Leu Thr Gly Pro Glu Ala Phe Glu Gly Tyr Ser
    50                  55                  60

Val Met Gln Ala Val Gln Ala Thr Met Ile Leu Ser Thr Ile Leu Ser
65                  70                  75                  80

Cys Ile Ser Phe Leu Ile Phe Leu Leu Gln Leu Phe Arg Leu Lys Gln
                85                  90                  95

Gly Glu Arg Phe Val Leu Thr Ser Ile Ile Gln Leu Met Ser Cys Leu
            100                 105                 110

Cys Val Met Ile Gly Ala Ser Ile Tyr Thr Asp Arg Arg Gln Asp Leu
        115                 120                 125

His Gln Gln Asn Arg Lys Leu Tyr Tyr Leu Leu Gln Glu Gly Ser Tyr
    130                 135                 140

Gly Tyr Ser Phe Ile Leu Ala Trp Val Ala Phe Ala Phe Thr Phe Ile
145                 150                 155                 160

Ser Gly Leu Met Tyr Met Ile Leu Arg Lys Arg Lys
                165                 170

<210> SEQ ID NO 2
<211> LENGTH: 5
<212> TYPE: PRT
<213> ORGANISM: Artificial Sequence
<220> FEATURE:
<223> OTHER INFORMATION: Synthetic sequence, CRAC sequence
<220> FEATURE:
<221> NAME/KEY: MISC_FEATURE
<222> LOCATION: (1)..(1)
<223> OTHER INFORMATION: Leu can also be Val
<220> FEATURE:
<221> NAME/KEY: MISC_FEATURE
<222> LOCATION: (2)..(2)
<223> OTHER INFORMATION: can be 1, 2, 3, 4 or 5 amino acids
<220> FEATURE:
<221> NAME/KEY: MISC_FEATURE
<222> LOCATION: (4)..(4)
<223> OTHER INFORMATION: can be 1, 2, 3, 4 or 5 amino acids
<220> FEATURE:
<221> NAME/KEY: MISC_FEATURE
<222> LOCATION: (5)..(5)
<223> OTHER INFORMATION: Lys can also be Arg

<400> SEQUENCE: 2

Leu Xaa Tyr Xaa Lys
1               5
```

```
<210> SEQ ID NO 3
<211> LENGTH: 5
<212> TYPE: PRT
<213> ORGANISM: Artificial Sequence
<220> FEATURE:
<223> OTHER INFORMATION: Synthetic sequence, CARC sequence
<220> FEATURE:
<221> NAME/KEY: MISC_FEATURE
<222> LOCATION: (1)..(1)
<223> OTHER INFORMATION: Lys can also be Arg
<220> FEATURE:
<221> NAME/KEY: MISC_FEATURE
<222> LOCATION: (2)..(2)
<223> OTHER INFORMATION: can be 1, 2, 3, 4 or 5 amino acids
<220> FEATURE:
<221> NAME/KEY: MISC_FEATURE
<222> LOCATION: (3)..(3)
<223> OTHER INFORMATION: Tyr can also be Phe
<220> FEATURE:
<221> NAME/KEY: MISC_FEATURE
<222> LOCATION: (4)..(4)
<223> OTHER INFORMATION: can be 1, 2, 3, 4 or 5 amino acids
<220> FEATURE:
<221> NAME/KEY: MISC_FEATURE
<222> LOCATION: (5)..(5)
<223> OTHER INFORMATION: Leu can also be Val

<400> SEQUENCE: 3

Lys Xaa Tyr Xaa Leu
1               5
```